United States Patent [19]

Pellegrino et al.

[11] Patent Number: 5,609,152
[45] Date of Patent: Mar. 11, 1997

[54] PRONE POSITION STEREOTACTIC MAMMOGRAPHY NEEDLE BIOPSY APPARATUS AND METHOD FOR USING THE SAME

[75] Inventors: Anthony J. Pellegrino, New Fairfield; Milton Stoller, West Hartford, both of Conn.; Kenneth F. DeFreitas, Patterson, N.Y.; David D. Camarra, Fairfield; Anthony M. Scandura, Scotland, both of Conn.; Richard F. Schutz, Brewster, N.Y.; Jeffrey R. Storm, North Bend, Wash.

[73] Assignee: Thermotrex Corporation, San Diego, Calif.

[21] Appl. No.: 388,810

[22] Filed: Feb. 15, 1995

Related U.S. Application Data

[62] Division of Ser. No. 185,690, Jan. 24, 1994, Pat. No. 5,426,685, which is a division of Ser. No. 957,275, Oct. 6, 1992, Pat. No. 5,289,520, which is a continuation-in-part of Ser. No. 799,412, Nov. 27, 1991, abandoned.

[51] Int. Cl.$^6$ ........................................ A61B 5/05
[52] U.S. Cl. ..................... 128/653.1; 378/37; 128/754
[58] Field of Search ........................ 128/653.1, 662.05, 128/754; 606/130; 378/37, 87, 68, 208, 193, 195, 196; 5/601

[56] References Cited

U.S. PATENT DOCUMENTS

| | | | |
|---|---|---|---|
| 3,165,630 | 1/1965 | Bielat et al. | 378/37 |
| 3,556,081 | 1/1971 | Jones | 378/37 |
| 3,578,971 | 5/1971 | Lasky | 378/37 |
| 3,609,355 | 9/1971 | Schwarzer | 378/37 |
| 3,963,933 | 6/1976 | Henkes | 378/20 |
| 3,973,126 | 8/1976 | Redington | 378/17 |
| 4,051,380 | 9/1977 | Lasky | 378/37 |
| 4,099,880 | 7/1978 | Kano | 378/41 |
| 4,245,158 | 1/1981 | Burstein | 250/370.09 |
| 4,727,565 | 2/1988 | Ericson | 378/205 |
| 4,852,137 | 7/1989 | MacKay | 378/62 |
| 4,873,708 | 10/1989 | Cusano | 378/19 |
| 4,875,478 | 10/1989 | Chen | 378/20 |
| 4,878,234 | 10/1989 | Pfeiffer | 378/40 |
| 4,890,311 | 12/1989 | Saffer | 378/99 |
| 4,905,265 | 2/1990 | Cox | 378/99 |
| 4,926,452 | 5/1990 | Baker et al. | 378/99 |
| 4,930,143 | 5/1990 | Lungren | 378/37 |
| 4,987,307 | 1/1991 | Rizzo | 378/191 |
| 5,018,176 | 5/1991 | Romeas et al. | 378/37 |
| 5,050,197 | 9/1991 | Virta et al. | 378/37 |
| 5,056,523 | 10/1991 | Hotchkiss | 378/37 |
| 5,078,142 | 1/1992 | Siczek | 378/37 |
| 5,107,843 | 4/1992 | Aarnio et al. | 128/662.05 |
| 5,142,557 | 8/1992 | Toker et al. | 378/37 |
| 5,199,054 | 3/1993 | Adams et al. | 378/21 |
| 5,409,497 | 4/1995 | Siczek et al. | 128/653.1 |
| 5,415,169 | 5/1995 | Siczek et al. | 606/130 |

OTHER PUBLICATIONS

Bolmgren, et al; Stereotaxic Instrument for Needle of the Mamma; Am. J. Roent. 129:121–125, Jul. 1977.
Nordenstrom, *Breast*, Ch. 5 1981.
Fischer Mammotest Advertising Brochure Aug. 1989.

*Primary Examiner*—Marvin M. Lateef
*Assistant Examiner*—Brian L. Casler
*Attorney, Agent, or Firm*—Ware, Fressola, Van Der Sluys & Adolphson

[57] ABSTRACT

A patient-supporting table for performing prone stereotactic mammographic biopsy procedures having a platform with an aperture positioned so as to divide the platform into two supporting portions is disclosed. Each of the supporting portions of the platform are sufficient to support at least a patient's torso and legs. The supporting portions of the platform enable a patient's breast to be pendulantly presented in two different orientations with respect to the aperture which further enables 360° access to a pendulantly presented breast by stereotactic mammography and biopsy apparatus which have rotation ranges substantially less than 360° but more than 180° relative to the aperture.

10 Claims, 18 Drawing Sheets

FIG. I

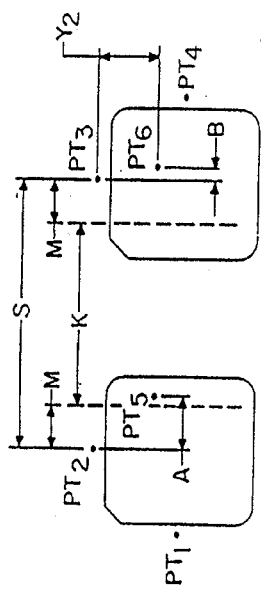
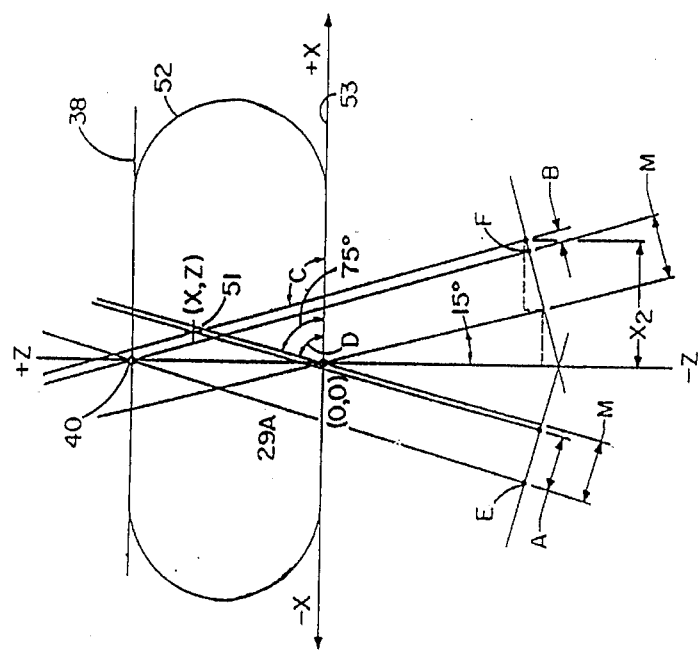
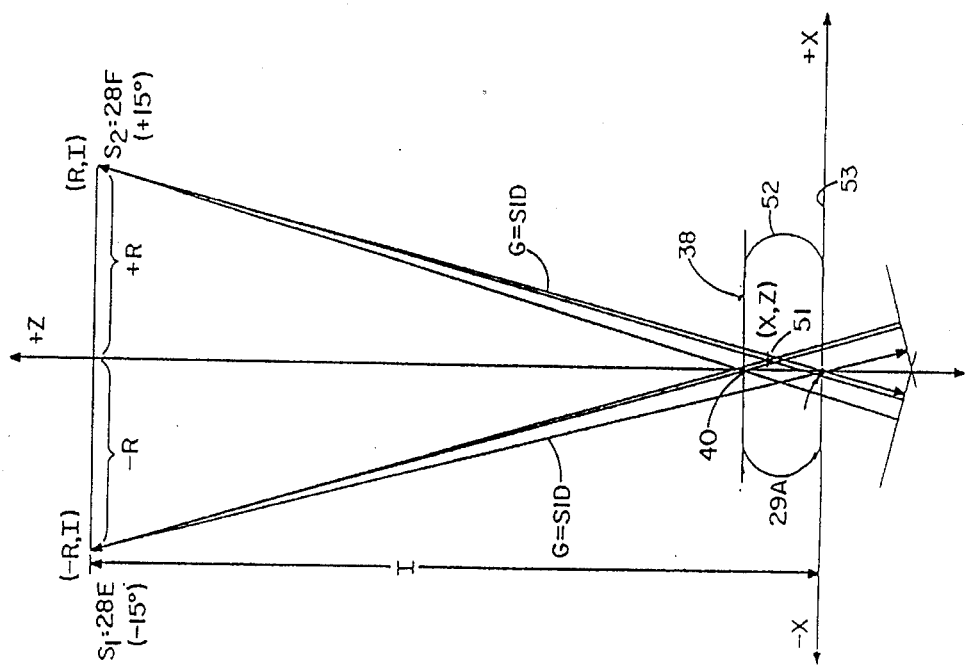

5,609,152

PRONE POSITION STEREOTACTIC MAMMOGRAPHY NEEDLE BIOPSY APPARATUS AND METHOD FOR USING THE SAME

CROSS REFERENCE TO RELATED APPLICATION

This is a divisional application of U.S. Ser. No. 08/185,690 filed Jan. 24, 1994 now U.S. Pat. No. 5,426,685 issued on Jun. 20, 1995, which is a divisional application of U.S. Ser. No. 07/957,275 filed Oct. 6, 1992 now U.S. Pat. No. 5,289,520, issued on Feb. 22, 1994, which is a continuation-in-part of co-pending application Ser. No. 07/799,412, filed Nov. 27, 1991, now abandoned. The disclosures of the above listed parent applications are hereby incorporated by reference.

This invention relates to a patient-supporting table and associated equipment for X-ray mammography and stereotactic needle biopsy of breast tissue suspected to contain lesions requiring radiographic evaluation.

RELATED ART

Since the publication of an article entitled "Stereotaxic Instrument for Needle Biopsy of the Mamma" by Jan Bolmgren et al, published in the American Journal of Roentgenology Vol. 129, Page 121 in July 1977, needle biopsy of breast lesions to minimize unnecessary surgical invasion of the patient's tissue has achieved increasing acceptance. Guidance of the biopsy needle by stereotactic X-ray exposures traditionally required development of the two X-ray film images and their comparison to determine the X, Y and Z coordinates of the lesion in question. Insertion of the biopsy needle via a carefully placed needle guide directed toward the lesion site could be verified only by additional stereo X-ray film exposures.

Mammograms made while the patient sits erect before the X-ray equipment may introduce unavoidable patient movement and resulting inaccuracy, while conventional tables supporting the patient in the prone position with the breast depending through a suitable aperture in the table generally require a patient's arms to be raised, tensing arm muscles, straining or distorting the breast tissue and again introducing inaccuracies. In addition, relatively flat and rigid tables often impose undue stress and discomfort on the patient's joints and vertebra, inducing undesired restless movements.

SUMMARY OF THE INVENTION

The unique prone position mammography tables of the present invention provide comfortable support for the prone patient, with a front edge portion being removable, permitting the patient's arm and shoulder to be lowered to more normal positions and thus minimizing patient discomfort and involuntary movements, leaving the patient normally relaxed during the procedure. In addition, a central concave torso depression formed in these tables exposes the maximum volume of breast tissue for X-ray examination.

Furthermore, the central concave torso depression encircling the breast-receiving aperture is positioned at the center of a longer-than-normal table having an extensible footrest at each end, which is supported by a rear pedestal opposite the removable front edge portion. The X-ray tube and the biopsy needle guide are thus afforded access to the patient's pendulant breast from all possible angles, over a range of more than 360°.

With this invention, accurate placement of the biopsy needle is further achieved via electronic imaging of the tissue X-rayed utilizing charge coupled devices or CCDs, with computer enhancement software designed to increase the sharpness of contrast between portions of the image most indicative of particular lesion structures of possible interest. This CCD-based imaging system offers such advantages in visualization and differentiation of nonpalpable lesions that contrast resolution and system sensitivity exceed that available with conventional screen or film X-ray mammography, often permitting definitive diagnosis of equivocal findings without the need for biopsy. Visualization capabilities are further increased by electronic image processing techniques to enhance contrasts. Delays in film development and evaluation are eliminated by the systems of the present invention, providing virtually instant confirmation of proper biopsy needle placement, reducing patient discomfort during this critical phase of the procedure.

This virtually real time imaging of the stereotactic X-ray images, and their computer enhancement, are preferably facilitated by an optical system interposed in the position normally occupied by the X-ray film cassette. This preferred optical system employs a phosphor screen exposed to the arriving X-rays passing through the breast tissue, and the image created on the phosphor screen by the arriving X-rays is reflected by a mirror surface provided by a pellicle reflector, comprising an extremely thin sheet of select optical grade nitrocellulose, on the order of five to nine microns in thickness, stretched like a drumhead over a black anodized flat metal frame and bonded to the precision lapped edge of the frame. The X-radiation passes directly through this thin film to the phosphor screen, while the visible light image of the phosphor screen is reflected from the film's underside directly toward the camera lens, due to a reflective coating of metallic material such as aluminum silicate, deposited on the underside of the thin film. Suitable coatings produce up to nearly sixty percent reflectance, depending upon wavelength. In a preferred embodiment, a second flat mirror surface redirects the reflected image, thereby producing a compact folded optical system conveniently enclosed in a light-tight housing occupying very little more space than conventional X-ray film cassettes and associated film holder structures. The preferred camera is Peltier cooled, and incorporates a rectangular CCD format with one thousand or more pixels along each orthogonal edge.

The comfortable table for supporting the patient in the prone position with minimum distortion of normal breast configuration cooperates with the stereotactic X-ray projection system mounted directly under the table. When desired, the folded CCD imaging system replaces the normal X-ray film cassette, and the unique software enhances the contrast and sharpness of the resulting virtually real time image. Preferably the image-receptor and the X-ray tube are mounted on the same angularly movable C-arm, assuring that the X-ray image is always perpendicular to the optic axis of the arriving X-rays. This permits a bucky grid to have all of its grid planes permanently aligned with the X-ray source, minimizing lateral scatter radiation and producing X-ray images of maximum sharpness and clarity.

These aspects of the invention all combine to produce a highly useful prone patient-supporting table for X-ray mammography and an effective stereotactic mammography system serving to minimize patient discomfort and trauma while permitting highly precise location and needle biopsy of suspected breast lesions, avoiding invasive surgery in a large number of cases.

Thus, a principal object of the present invention is to provide highly precise mammography systems providing uniquely accurate images of the observed breast structures of the patient.

Another object of the invention is to provide such systems incorporating prone patient supporting tables designed to expose the breast for mammographic examination while also assuring its undistorted orientation and the optimum comfort and relaxation for the patient during the procedure.

Still another object of the invention is to provide such systems with the capability for accurate guidance of needle biopsy procedures employing virtually real time electronic imaging and needle placement verification, eliminating delays for film cassette loading, changing, unloading, developing and evaluation.

A further object of the invention is to provide such systems which are capable of stereotactic imaging of the maximum volume of the patient's breast tissue to provide three dimensional location of internal lesions or other internal sites requiring surgical examination.

A still further object of the invention is to provide folded CCD optical systems taking advantage of large CCD devices to provide extremely high resolution images of the patient tissue sites under study.

Another object of the invention is to provide digital X-ray image processing techniques using window and level manipulation, region of interest analysis, filters and edge enhancement, providing definitive X-ray diagnosis in many cases.

Other objects of the invention will in part be obvious and will in part appear hereinafter.

The invention accordingly comprises the features of construction, combinations of elements, and arrangements of parts which will be exemplified in the constructions hereinafter set forth, and the scope of the invention will be indicated in the claims.

THE DRAWINGS

For a fuller understanding of the nature and objects of the invention, reference should be made to the following detailed description taken in connection with the accompanying drawings in which:

FIG. 8 is a schematic diagram of the stereotactic mammography procedure of this invention, comparing the X-radiation paths through a suspect lesion and a reference point on the compression plate for two angularly offset tubehead source positions, when the image receptor pivots with the tubehead on the C-arm;

FIG. 9 is a fragmentary enlarged schematic diagram showing the lower end of FIG. 8 in more detail;

FIG. 10 is a schematic diagram of the two images produced at the image receptor by X-radiation from the same two source positions;

BEST MODE FOR CARRYING OUT THE INVENTION

Three principal components or sub-assemblies are incorporated in the preferred embodiments of the present invention. These are the adjustable and versatile prone patient supporting table shown in FIGS. 1–7C, the novel CCD imaging folded optical system shown in FIGS. 11, 12 and 15–17, and the image enhancement and data display monitor systems providing high resolution and nearly real time image displays in the systems of the invention as illustrated schematically in FIG. 18.

Figure 1:
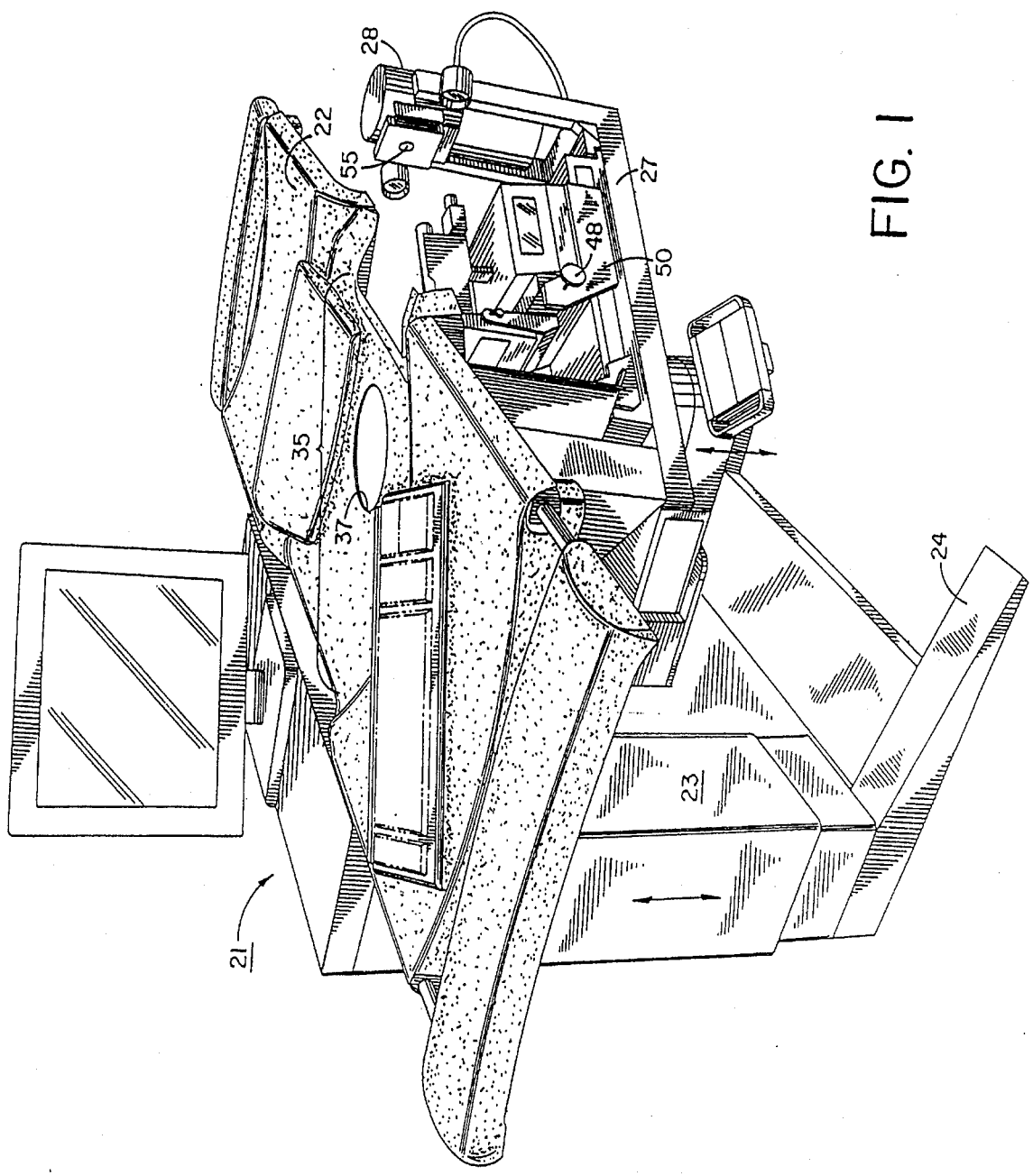
FIG. 1 is a top perspective view of the prone patient supporting mammography table of the present invention.

Patient supporting table 21 comprises platform 22 on which the patient rests in a prone position, supported by a rear pedestal 23 upstanding from the rear portion of a base 24, all as shown in FIG. 1. Pedestal 23 preferably incorporates table elevating means to raise and lower the table within limits for convenience of the patient and attending personnel.

Protruding forward over the lower part of base 24 from the front face of pedestal 23 is a ledge 26 sturdily constructed to provide underlying support for an angularly movable "C-arm" 27. Arm 27 is shaped like a letter C lying on its back, with one upstanding end mounting the X-ray source or mammography unit tube head 28. The pivot axis 29, about which C-arm 27 is mounted for angular rotation relative to ledge 26, is close to the opposite upstanding end of the C-arm 27, and this upstanding end incorporates either X-ray film cassette 31 or CCD sensor folded optical system 32 enclosed in a light-tight housing and shown schematically in FIGS. 11 and 12, and in the perspective top view of FIG. 15.

Figure 2:
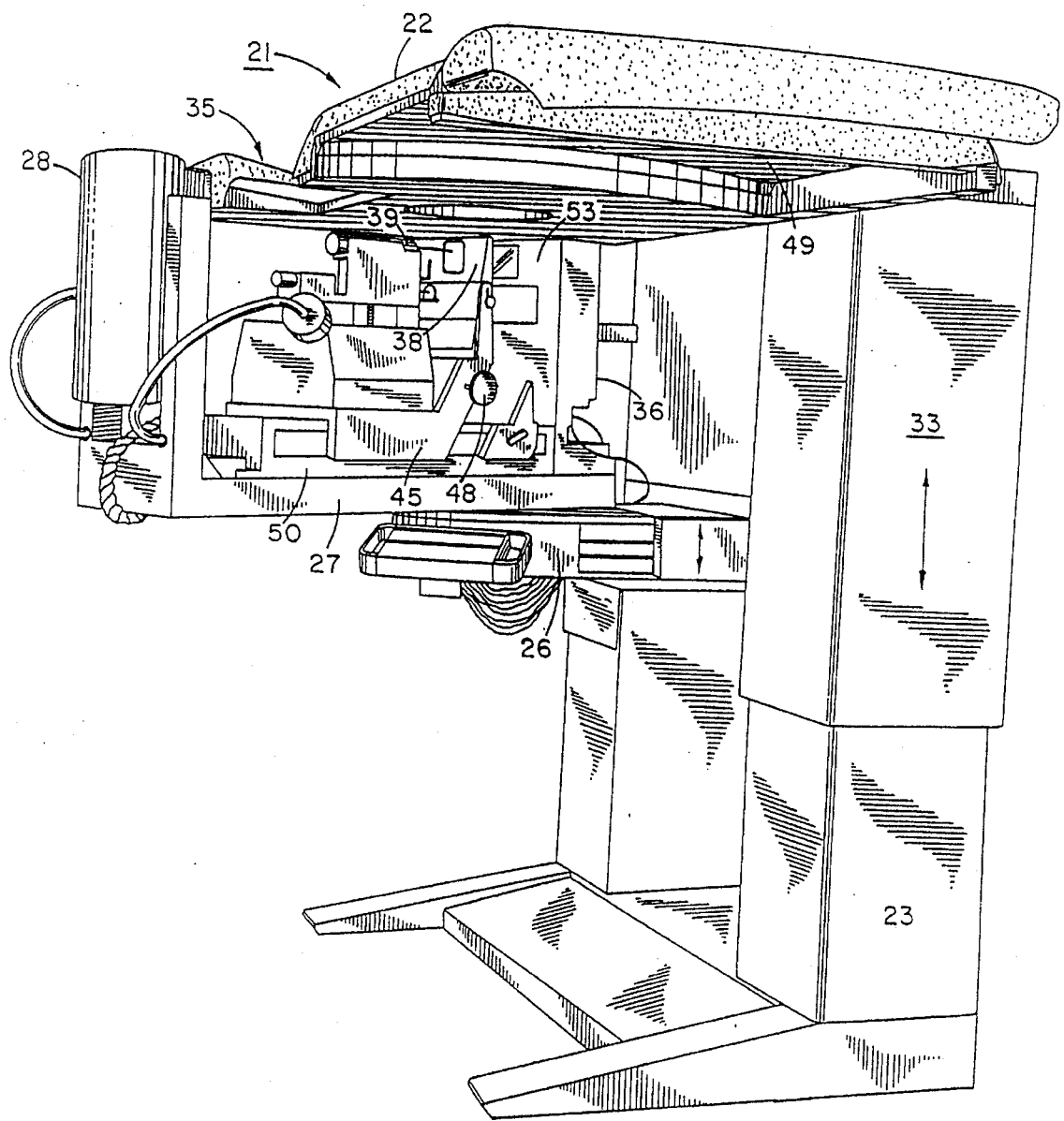
FIG. 2 is an end perspective view of the same table showing the base, pedestal and angularly movable C-arm carrying the X-ray tube and the image receptor, as well as the separate compression arm carrying compression plates and needle guide.
Figure 3:
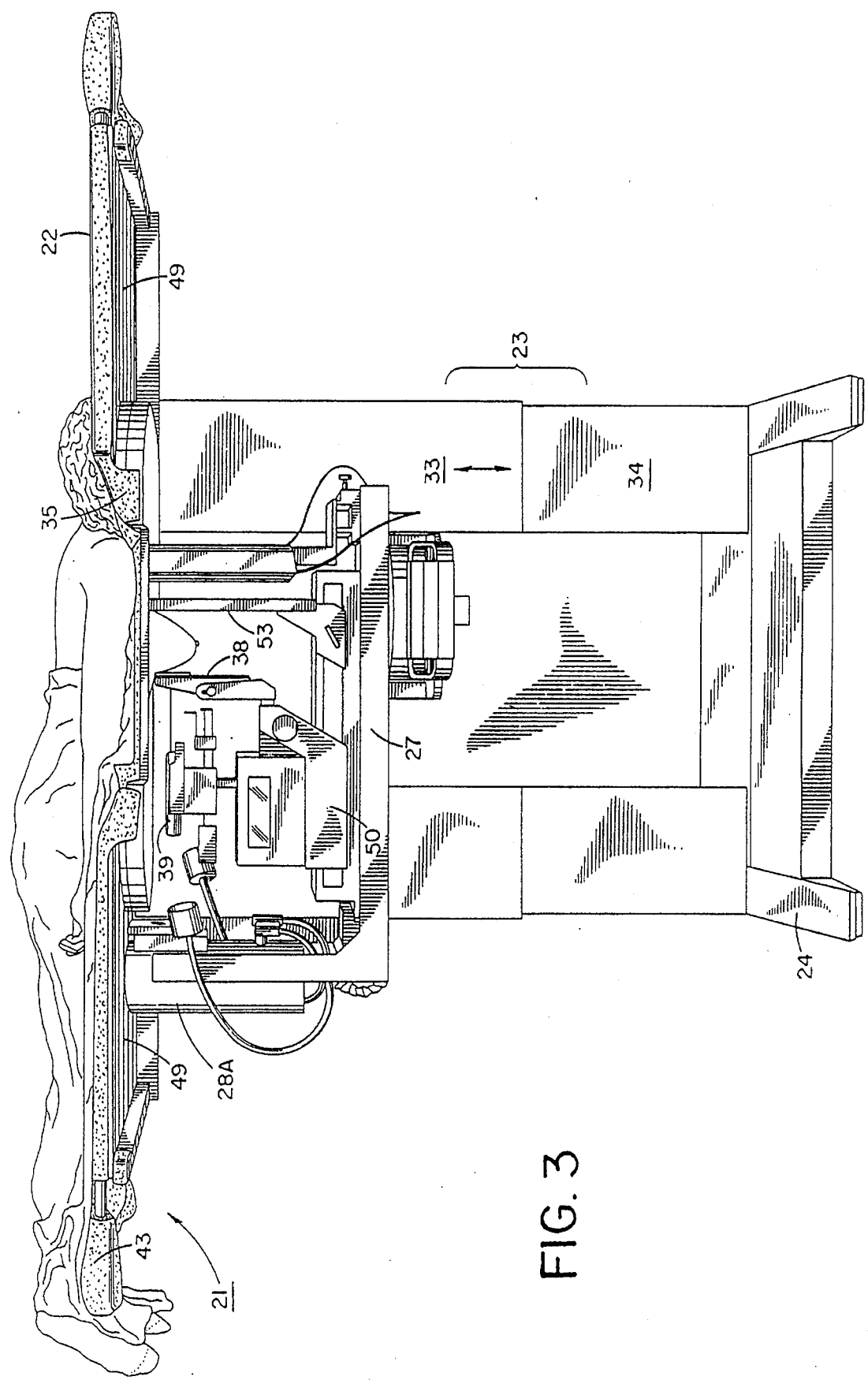
FIG. 3 is a front elevation view of the same table supporting a prone female patient at maximum elevation above the floor, delivering X-radiation to the underside of the breast, toward the table's right end.

As indicated in FIGS. 1–3, the upper portion 33 of pedestal 23 supporting the table platform 22 at its upper end and the ledge 26 at its lower end is capable of vertical downward movement from the raised position shown in FIG. 3 to a lowered position in which the ledge 26 is close to base 24, shown in FIG. 1. This vertical adjustment motion is provided by telescoping upper pedestal portion 33 over the underlying lower pedestal portion 34 shown in FIG. 3.

Further adjustability of the system is provided by separate vertical adjustment of ledge 26 relative to upper pedestal 33.

Ideally, the uppermost position 28A of tubehead 28 places it within the underside recess 49 formed in table platform 22 (FIG. 3) with the opposite end of the C-arm 27 comprising the image receptor 36, carrying either the X-ray film cassette 31 or the optical system 32, preferably being closely positioned adjacent the underside of table 22 as shown in FIG. 3, in order to bring the X-ray beam and the image receptor as close as possible to the chest wall of the patient lying prone, face down on platform 22.

Figure 4:
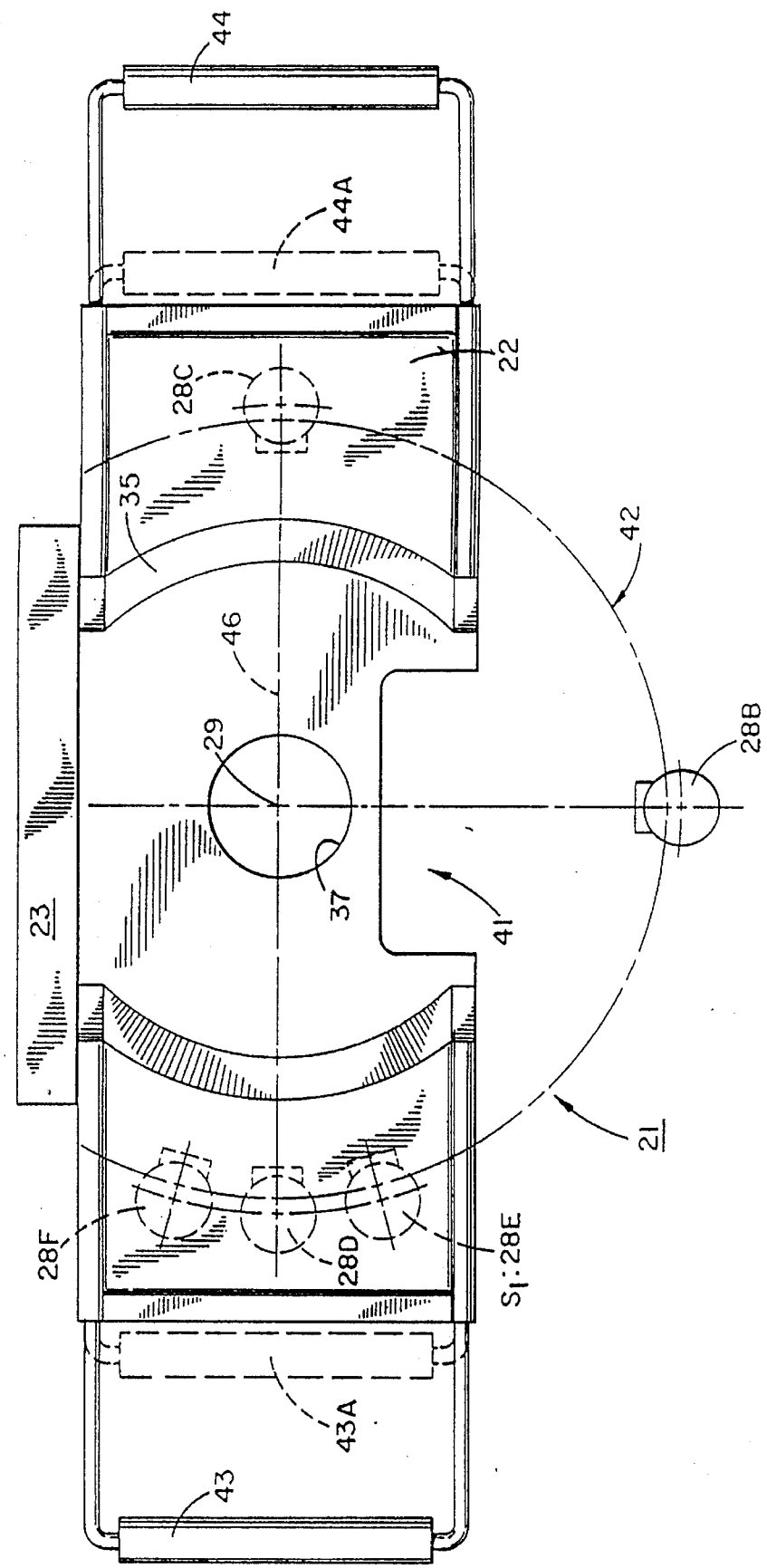
FIG. 4 is a schematic top plan view of the table showing the range of X-ray tube positions made possible by the rear pedestal construction of the unit.
Figure 5:
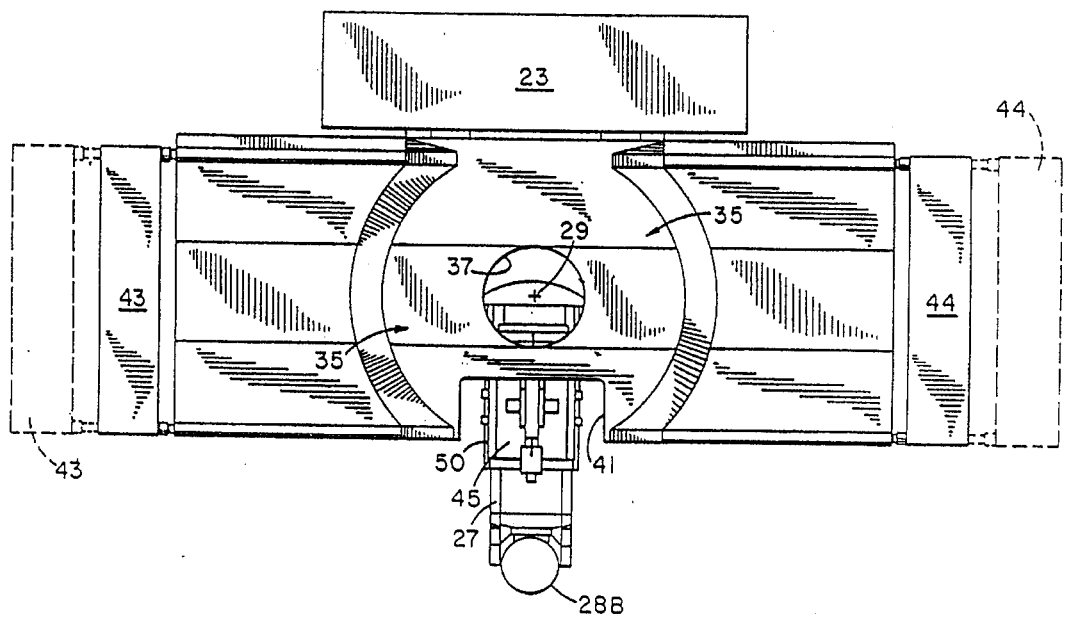
FIG. 5 is a top plan view of the table of FIGS. 1–3, with the C-arm positioned for delivering X-radiation from the side of the patient.

As shown in FIGS. 1, 4 and 5, a central aperture 37 is provided in the central portion of platform 22 accommodating one or both of the female patient's breasts depending therethrough as the patient lies face down on platform 22. Since image receptor 36 is relatively thin, as shown in FIGS. 3 and 5, and is positioned close to the pivot axis 29 about which the C-arm moves angularly, the pivoting movement of C-arm 27 about axis 29 allows the image receptor 36 to be positioned between the patient's breasts, or against the underside of either breast, by making minor adjustments in the position of axis 29 relative to ledge 26.

A fixed compression plate 53 and a compression paddle 38 movable toward and away from plate 53 are mounted above the C-arm 27 on an independently pivoted compression arm 50. Compression paddle 38 may be considered a biopsy compression device, since it incorporates both a transparent portion permitting X-rays to pass through it toward the patient's breast and image receptor 36, and a central needle access aperture. The compression arm 50 also incorporates mechanism for attaching a needle guide 39 for performing a needle biopsy without releasing the breast from the compression plate, thereby assuring that the target lesion coordinates determined by the original stereotactic measurements will be maintained upon insertion of the needle to reach the same target lesion coordinates.

The preferred form of table 22 shown in FIGS. 1 through 6 incorporates an additional useful feature, a central concave torso depression 35 surrounding the central aperture 37. Depression 35 provides comfortable support for the prone patient's head, shoulders and torso, with her hips and legs extending either to the right or to the left over the slightly higher end portions of table 22, which may also incorporate the footrests 43 and 44 if desired.

The central position of aperture 37, and the footrests 43 and 44 at both ends of the support tables 22 or 22A, provide double the 210° range of available X-ray projection angles indicated in FIG. 4, a range of some 420°. No conventional mammography tables are known to afford such a wide range of projection angles.

The slight elevation of the patient's hips by depression 35 maintains the normal relaxed curve of the patient's vertebra, while presenting the maximum possible volume of breast tissue through aperture 37 for X-ray examination. In addition, the slight elevation of the ends of table 22 outside of the central depression 35 provides the underside recess 49 encircling aperture 37, with vertical clearance for the upper end of X-ray tubehead 28 under table 22. This permits the focal point source FP of X-radiation to be elevated to a level nearly in tangent coincidence with the lower rim of aperture 37, providing desirable exposure of the maximum volume of the patient's pendulant breast tissue for examination.

The front edge of platform 22 beside aperture 37, opposite pedestal 23, is preferably formed as a removable panel 41, providing unimpeded access beneath platform 22 for the radiologist and technicians, and permitting the patient's arm to be lowered through the open space left by the removal of the panel 41 (FIG. 4) bringing her shoulder comfortably down toward the level of aperture 37 (FIG. 3) and minimizing any distortion or stretching of the breast pendulant through aperture 37.

Different positions of tubehead 28 produced by angular movement of C-arm 27 are illustrated in FIGS. 3–6, along the circular arcuate path 42 shown in FIG. 4. In the outermost tubehead position 28B, shown in FIG. 4 and FIG. 5, X-radiation projected toward axis 29 will approach a lesion from the lateral aspect of the right breast or the medial aspect of the left breast if the patient's head is positioned to the right on platform 22, as in FIG. 3. The footrest 43 at the left end of platform 22 is preferably extended to support the patient's legs in this position, while the footrest 44 at the right end of platform 22 is preferably retracted toward the table end to the dash line position 44A shown in FIG. 4. With the patient's head placed to the left of axis 29 in FIG. 4 and the footrest 44 being extended to its solid line position at the right end of platform 22, X-radiation from tubehead position 28B approaches the lateral aspect of the left breast or the medial aspect of the right breast. At either axial position, 28C near the right end of platform 22, or 28D near the left end of platform 22, the X-radiation approaches the breast from either above or below, with the image receptor 36 being positioned on the opposite side of the breast and the compression plate 53 and paddle 38 assuring that the patient is comfortably positioned with no risk of unexpected movement during the procedure.

In most cases, the tubehead 28 delivering X-rays to the patient will be positioned at the patient's head end of platform 22 with image receptor 36 and compression plate 53 being positioned on the underside of the pendulant breast and the compression paddle 38 being positioned on the upper side of the breast, both mounted on compression arm 50, which also provides support for needle guide 39 from this upperside when required. However, the presence of a lesion near the underside of the breast may indicate that the reverse orientation is preferred for minimum trauma, as indicated in FIG. 3, with the needle guide 39 and compression paddle 38 being positioned on the underside of the breast with the X-ray tubehead 28 being positioned beyond compression plate 53 on the upper side of the breast. In this position, the entry of the biopsy needle via needle guide 39 attached to compression paddle 38 into the underside of the breast tissue offers the minimum path length for access to the lesion, and this position may be preferred by many patients to assure that any needle scar will be on the underside of the breast where it is less easily observed.

Two additional tubehead positions 28E and 28F are also shown in FIG. 4, these being respectively displaced angularly by approximately 15 degrees counterclockwise and 15 degrees clockwise, which are typical angular displacements for stereotactic mammography. However, lesser angular amounts, of 10 degrees for .example, on each side of the longitudinal axis 46 of platform 22 can be used if desired, to assure that the stereoscopically displaced images both fall on the desired portion of the image receptor, whether it be X-ray film in a film cassette 31 or the electronic imaging optical system 32 illustrated in the figures. Stereoscopic displacement of the lesion image may place it near the periphery of the total image plane in particular lesion orientations, and for this reason, a lesser stereo displacement of the positions 28E and 28F may be indicated.

Figure 7C:
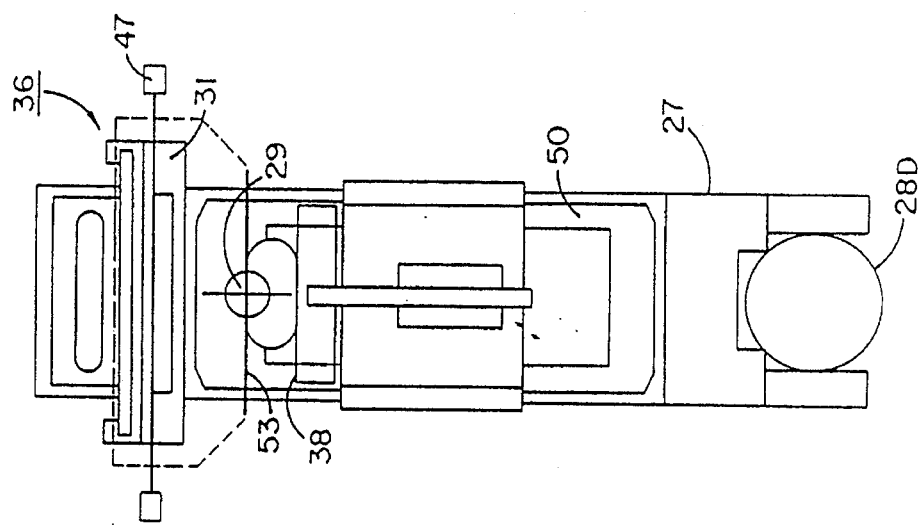
FIGS. 7A, 7B and 7C are-corresponding successive fragmentary top plan schematic views showing the compression arm carrying the breast compression plates and needle guide in a fixed position beneath the table, while the underlying C-arm carrying the X-ray tube and image receptor is moved to different angular positions.
Figure 7B:
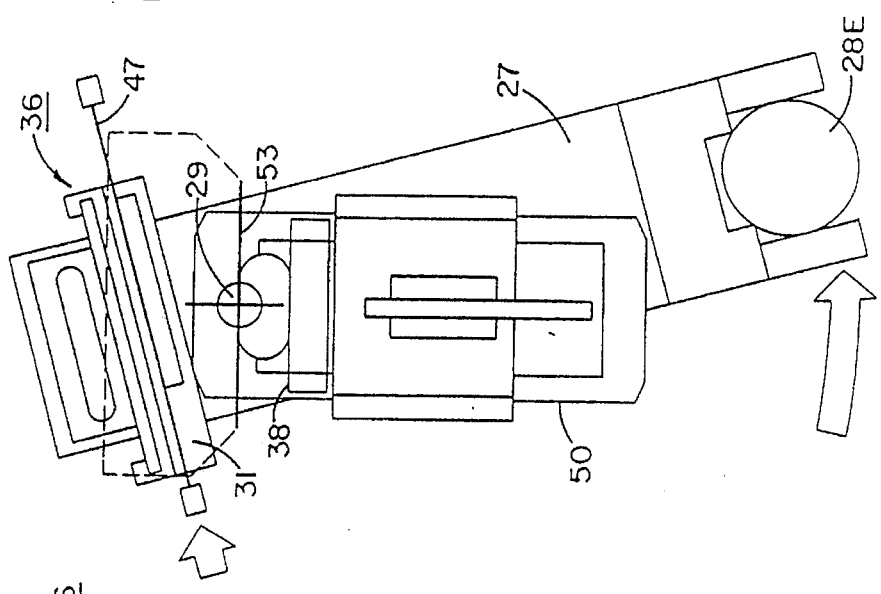
Figure 7A:
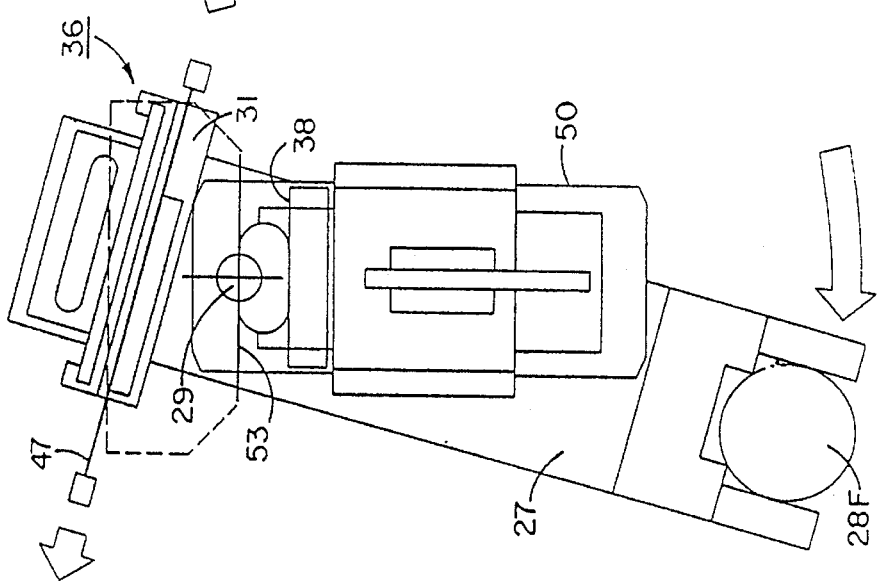

When the film cassette 31 is utilized at the image receptor 36 in stereotactic mammography, the cassette 31 may be provided with a film position shift lever 47, shown in FIGS. 7A–7C, and movement of this lever shifts the film cassette position so that stereo exposures at plus 15 degrees and minus 15 degrees angular displacement from axis 46 will be exposed side by side on the X-ray film. While the patient remains on platform 22 and the compression paddle 38 remains in position, the cassette may be removed and the film developed and examined to provide actual coordinates of the target lesion for needle biopsy. When the needle guide 39 is placed in position and the needle is inserted into the predetermined target tissue location, a new film cassette 31 may be placed in position on receptor 36 and two more stereo mammograms may be made to assure that the tip of the needle is at the desired location in the target lesion. Removal and development of this second cassette verifying the needle tip location thus permits any final adjustments required, and the needle biopsy may then be completed immediately.

X-, Y- and Z- axis indexing of needle guide 39 relative to the patient's breast tissue is provided by linear motorized adjustments mounted on an indexing carriage 45 movably mounted on linear bearings on the compression arm 50 pivoted on ledge 26 above pivoting tubehead C-arm 27. An indexing knob 48 cooperating with a timing belt or endless chain drive moves carriage 45 and compression paddle 38 into gentle compressive contact with the patient's breast 52, clamping it gently but firmly against the fixed breast compression plate 53. If fine needle biopsy is required, X, Y or Z control knobs on carriage 45 permit the operator to position the needle guide 39, adjusted for biopsy as required by the lesion coordinates found by stereotactic X-ray observations.

For convenience of notation, the X-axis is horizontal, extending toward pedestal 23; the Y-axis is vertical, extending upward toward the patient, and the Z-axis extends horizontally, parallel to table platform 22, toward X-ray tubehead source 28. The "pivot point" where pivot axis 29 intersects the X-Z plane passing through source focal point FP, is taken as the origin or zero-point for X, Y and Z values.

When the electronically enhanced CCD sensor optical system 32 is employed in place of the film cassette 31, a much shorter time is required for completion of the entire procedure. For example, the stereotactic procedure just described with two X-ray film cassettes customarily takes between 20 and 70 minutes during which time the patient must remain in the same position face down on the mammography table. With the electronic imaging systems incorporated in the preferred embodiments of the present invention, the digital image data received and processed in the system shown schematically in FIG. 18 ideally permits the mammography, the needle placement, the X-ray verification of needle location and the needle biopsy all to be completed within a period of one to two minutes, and certainly within a period far less than the 20 to 70 minutes normally experienced with customary X-ray film cassettes in stereotactic mammography. By minimizing the length of time a patient is required to remain in the same prone position, the patient's comfort and also the patient's relative immobility will be enhanced, minimizing inaccuracies which might be unavoidable if a patient were expected to lie still in the same position for a long period of time.

In addition to the very short time consumed by needle or core biopsy procedures when digital stereo CCD imaging is employed, there is a further important advantage achieved by the prone stereo mammography tables of this invention. As shown in FIG. 4, table 22 projects forward and is supported cantilever-fashion along its rear edge by rear pedestal 23. The wide clear open space under table 22 provides ample room for X-ray tubehead 28 to move pivotally through the infinite range of positions including those shown in the FIGURES: left longitudinal positions 28A or 28D (FIGS. 3, 4); stereo-offset positions 28E or 28F (FIG. 4); lateral position 28B (FIGS. 4, 5) and right longitudinal position 28C (FIGS. 4, 6).

Thus for a patient lying with her feet on left footrest 43, a range of 180°+15°+15° or 210° of right side tubehead positions are all available. If the same patient lies with her feet on right footrest 44, the full range of 210° of left side positions are equally available. Thus for the same patient, not just a 360° range but actually a 420° range of tubehead positions is readily available.

Figure 6:
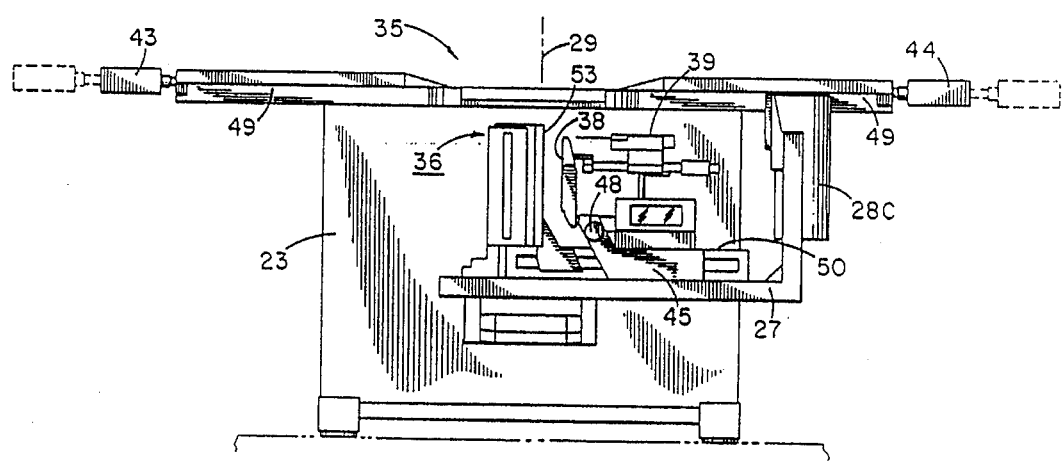
FIG. 6 is a schematic front elevation view of the same table, with the C-arm positioned for delivering X-radiation toward the table's left end.

The "gull-wing" longitudinal cross-section of table 22, best seen in FIGS. 3 and 6, with the shallow conical central depression 35 surrounding aperture 37, allows maximum patient comfort and excellent positioning of the pendulant breast to be examined, and also provides an added advantage over this entire 420° range. This is because both slightly raised "gull-wing" ends of table 22 create underside recesses 49 (FIGS. 2, 3 and 6), and X-ray tubehead 28 can thus be moved pivotally around the entire front 210° arcuate periphery of aperture 37 with its upper end projecting into recess 49. The tubehead's X-ray projection portal 55 (FIG. 1) positioned several inches below its uppermost end thus delivers its X-ray beam along a projection axis G=SID (FIG. 8) passing through a pivot axis 29 and perpendicular to image receptor 36, closely grazing the underside rim of aperture 37. This permits the maximum volume of breast tissue to be presented for mammographic examination over the infinite range of projection angles just described, with ample working space for radiologist and technicians beneath table 22, as indicated in FIGS. 2 and 3, for example.

STEREOTACTIC IMAGING SYSTEM

Stereotactic imaging of breast tissue by projecting X-rays through the patient's compressed breast from two different source positions to produce two stereo images on an X-ray film is disclosed in detail in the Bolmgren article, supra, from the American Journal of Roentgenology for July 1977 and also in U.S. Pat. No. 4,727,565 to Ericson and 4,930,143 to Lundgren. Applicants' FIG. 13 shows a schematic diagram of such prior art two-source-position stereotactic X-ray mammography with a lesion 51 in the tissue of a patient's breast 52 compressed between a fixed compression plate 53 and an adjustable compression paddle 38, both of which are transparent to X-rays.

Figure 13:
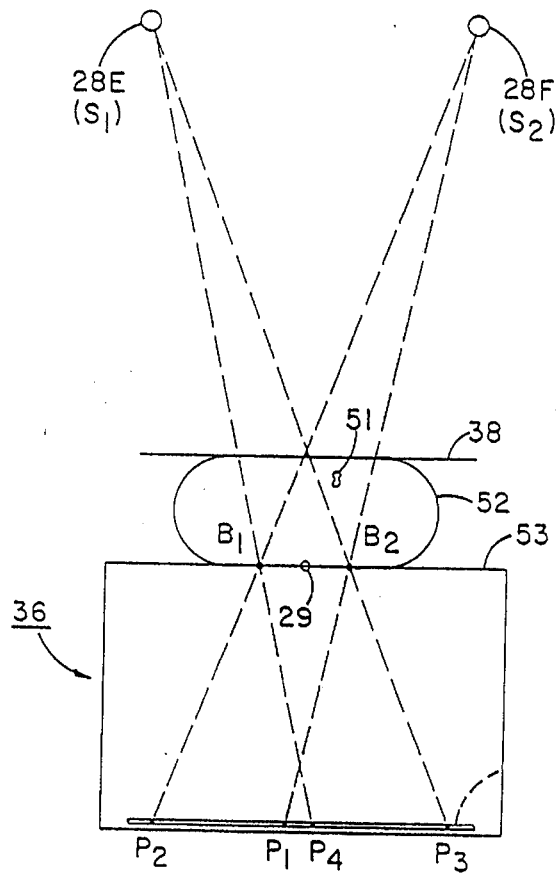
FIG. 13 is a top plan schematic view of the conventional stereotactic mammography procedure performed on prior art devices, showing the X-radiation arriving at significant angles of inclination from the perpendicular, introducing undesired image degradation, when the image receptor is stationary.

When image receptor 36 is stationary, the fixed compression plate 53 preferably coincides with the position of image receptor 36 shown in FIG. 13 and comprises the proximal surface of receptor 36.

When image receptor 36 of the present invention is mounted on the C-arm 27 for pivoting movement with the X-ray tubehead 28 source FP, as shown in FIGS. 2, 3 and 6–12, receptor 36 is spaced far enough behind pivot axis 29 to afford clearance for the desired angular pivoting motion.

An additional advantage of the mounting of the image receptor on the C-arm arises from the usefulness of bucky grids with divergingly slanted vanes to pass direct X-radiation from the source FP while blocking laterally scattered or secondary X-radiation which would otherwise reduce image sharpness. When the bucky grid is mounted on the image receptor 36 pivoting with the tubehead C-arm 27, its diverging vanes are aligned with source FP in all of its adjusted stereo positions shown in FIGS. 7A and 7B. By contrast, a stationary bucky mounted in front of the image plane in the prior art image receptor of FIG. 13 can have its vanes aligned with only one X-ray source point, interfering with some of the desired direct X-radiation projected from other, offset source points and seriously reducing the bucky's usefulness.

The determination of X-, Y- and Z- coordinates of suspect lesions is performed by calculating the equations of slope for the X-ray paths passing through the lesion and through a reference point 40 on the compression 38 to a first image plane for the first source position S1 or 28E (FIGS. 4, 8) and for the second source position S2 or 28F.

In FIGS. 8, 9 and 10, the coordinates of the suspect lesion 51 are X, Y and Z. Points 1 and 2 are the Y and X positions of the reference hole 40 image on the left image area in FIG. 10, produced when the source is at S2 or 28F. Points 3 and 4 are the X and Y positions of the hole 40 image on the right image area, produced when the source is at S1 or 28E. Points 5 and 6 are the images of the suspect lesion 51 in the two image areas of FIG. 10.

This method is based on finding the equations of the two source-to-image lines for the two lesion images. The intersection of the two lines provides the X, Y and Z coordinates, on the X-Y, Y-Z and X-Z planes.

Diagrammatic FIG. 8 shows the X-Z plane as viewed from below. The pivot point, where the pivot axis 29 passes through the X-Z plane, serves as the zero point for both X and Z values, for analytical purposes.

Diagrammatic FIG. 9 is an enlarged view of the portion of the same diagram around the pivot point.

The source-to-image lines for the image created when the tubehead source is in the left position (−15°), indicated by position S1 or 28E in the other figures is:

$$X - X1 = \frac{Z - Z1}{ML} \qquad X1 = -R; Z1 = I$$

$$Z = \text{distance from pivot point to lesion}$$

$$X = \frac{Z - I}{ML} - R \qquad [\text{Eq. 1}]$$

$$ML = \tan C = \tan\left(105° + \arctan\frac{M+B}{G}\right)$$

$$= \frac{\tan 105° + \frac{M+B}{G}}{1 - \tan 105° \times \frac{M+B}{G}}$$

Where

G=SID, the source-to-image distance

M=distance from projected pivot point to compression reference hole 40 images E, F (see FIGS. 8, 9 and 10).

B=distance between reference image (point 3) and lesion image (point 6).

The source-to-image lines with the source in the right half (or +15°) position S2 or 28F is:

$$X - X1 = \frac{Z - Z1}{MR} \qquad X1 = -R; Z1 = I$$

$$Z = \text{pivot point to lesion}$$

$$X = \frac{Z - I}{MR} + R \qquad [\text{Eq. 2}]$$

$$MR = \tan D = \tan\left(75° - \arctan\frac{M-A}{G}\right)$$

$$= \frac{\tan 75° - \frac{M-A}{G}}{1 + \tan 75° \times \frac{M-A}{G}}$$

A=distance between reference image (point 2) and lesion image (point 5).

Solving for Z: [EQ. 1]=[EQ. 2]

$$\frac{Z-I}{ML} - R = \frac{Z-I}{MR} + R$$

$$Z = \frac{2R}{\frac{1}{ML} - \frac{1}{MR}} + I$$

height (by similar methods using −15° image)

$$Z(\;) - Z1 = MT(X - X1)$$

$$MT = \tan\left(105° + \arctan\frac{M}{G}\right)$$

$$= \frac{\tan 105° + \frac{M}{G}}{1 - \tan 105° \times \frac{M}{G}}$$

$$Z(\;) = R \frac{\tan 105° + \frac{M}{G}}{1 - \tan 105° \times \frac{M}{G}} + I$$

$$\text{Lesion depth} = \frac{2R}{\frac{1}{ML} - \frac{1}{MR}} + I - RMT + I$$

$$= \frac{2R}{\frac{1}{ML} - \frac{1}{MR}} - RMT$$

Finding $X$:

$$(X + R)ML + I = (X + R)MR + I$$

$$XML + RML + I = XMR + RMR + I$$

$$X = -R\frac{(ML + MR)}{(ML - MR)}$$

Then $Y$:

$$\frac{X - X1}{X2 - X1} = \frac{Y - Y1}{Y2 - Y1}$$

$Y1 = Y(\text{source}) = 0$ $Y2$ is measured on film $PT3 - PT6$ (FIG. 10)

$$Y = (Y2 - Y1)\frac{(X - X1)}{(X2 - X1)} + Y1 \quad X1 = -R$$

$$= Y2\frac{(X - X1)}{(X2 - X1)}$$

$$= Y2\frac{(X + R)}{(X2 + R)}$$

$$X2 = (SID - FPD)\sin 15° + (M + B)\cos 15°$$

See FIG. 10

In FIGS. 8, 9 and 10,

| | |
|---|---|
| $M = \frac{1}{2}(S - K)$ | |
| K = FILM SHIFT | (74.5 mm) |
| G = SID | (743.0 mm) |
| FPD = FOCAL PT. − PIVOT POINT | (661.5 mm) |
| R = FOCAL SHIFT = FPD sin 15° | (171.2 mm) |
| I = FPD cos 15° | |

DIGITAL IMAGING SYSTEM

Figure 12:
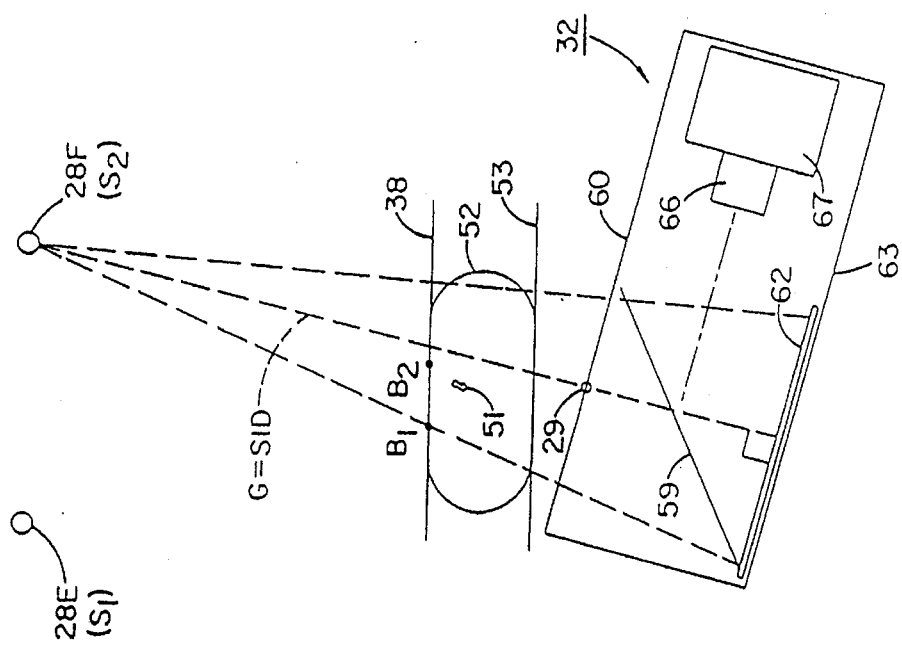
FIGS. 11 and 12 are schematic diagrams of the X-radiation paths for two angularly offset stereo tubehead source positions utilizing a folded CCD optical imaging system inserted in the position occupied by the X-ray film cassette in film mammography but with the digital CCD optical imaging system of FIGS. 13–17 pivoting with the tubehead.
Figure 11:
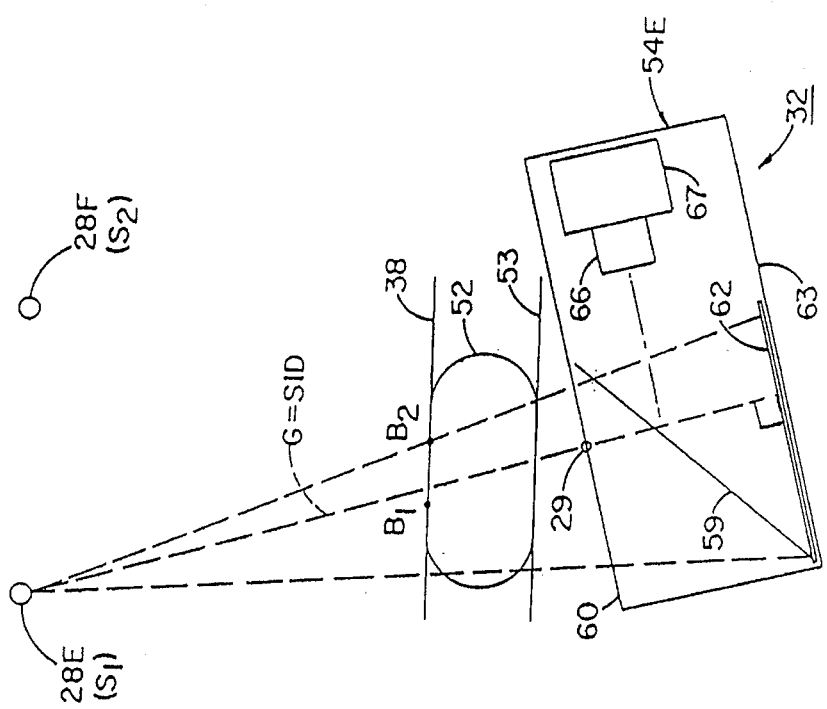
Figure 15:
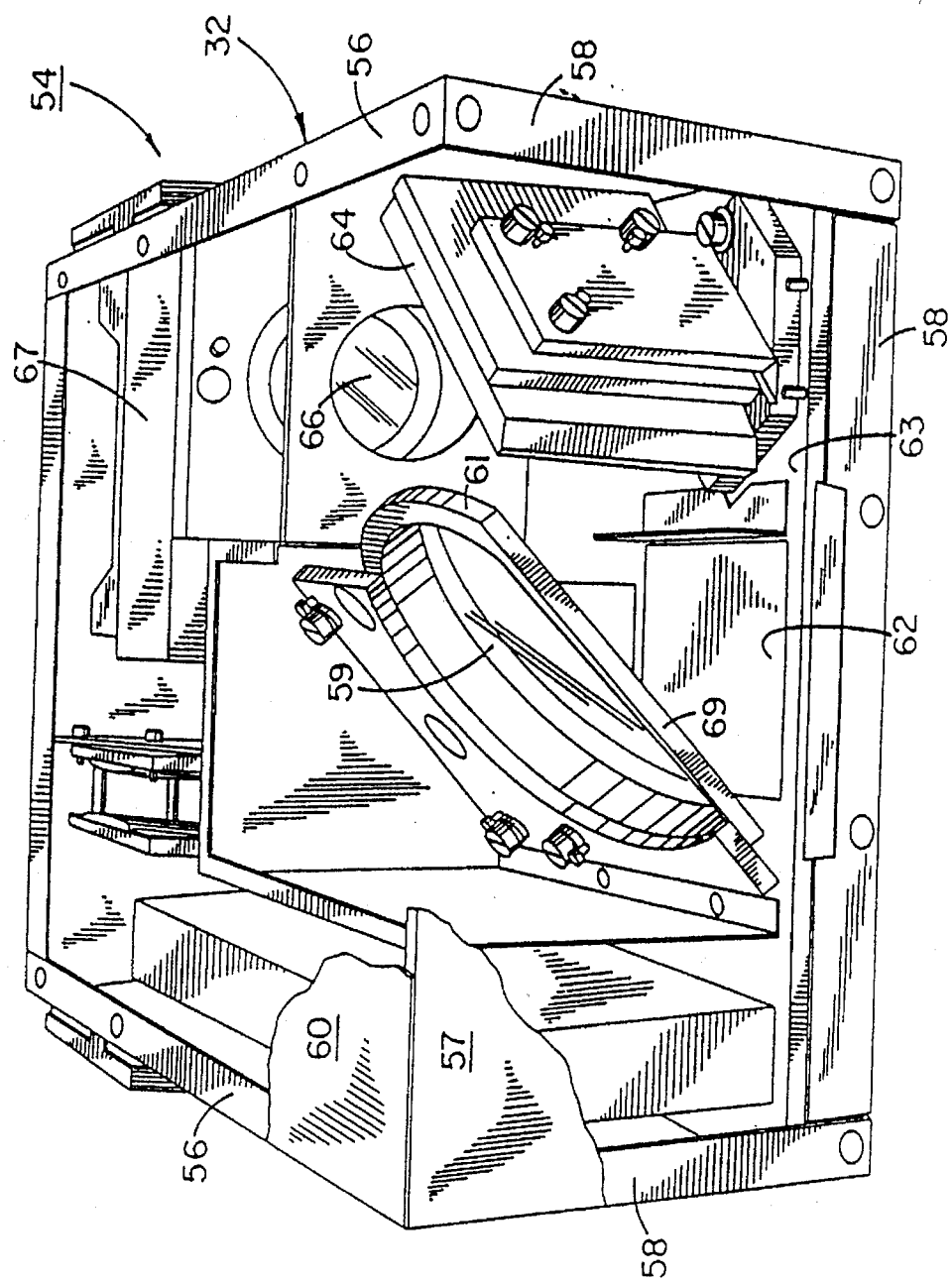
FIG. 15 is a perspective top view of the folded optical system employed in the stereotactic CCD imaging system of FIGS. 11 and 12, with a portion of the light-tight housing removed to reveal the location of the various components of the optical system.
Figure 17:
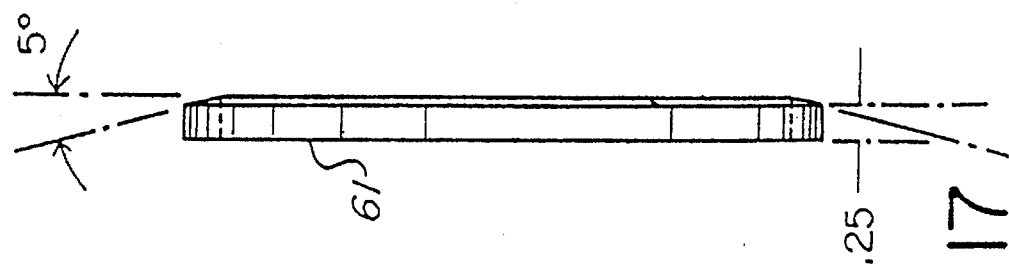
FIG. 17 is an edge elevation view of the same pellicle mirror.

The principal internal components of the folded optical system 32 are shown schematically in FIGS. 11 and 12, and in the cutaway top perspective view of FIG. 15, where the X-ray transparent cover plate 60 forming the proximal or front wall of housing 54 has been removed from its supporting proximal flanges 56, to reveal the internal structures inside housing 54. In the same manner, an upper housing panel 57 has been removed from its upper supporting flanges 58, thus revealing the internal structure of the optical system 32. Fragmentary broken away portions of panel 57 and cover plate 60 are shown at the left side of FIG. 15.

As indicated in FIGS. 11 and 12, radiation from the X-ray tubehead 28 passes successively through the X-ray transparent adjustable compression paddle 38, the patient's breast 52, the fixed compression plate 53, and then through a thin film pellicle mirror 59. This is a film of high tensile strength elastic membrane material such as nitrocellulose having a thickness ranging between 5 and 9 microns (micrometers), for example, stretched like a drumhead over a flat metal frame 61 (FIG. 15) and bonded to the precision lapped edge of this frame. The thin pellicle film is virtually transparent to X-radiation which passes directly through it to impinge upon the underlying phosphor screen 62 mounted on the image plane at the rear wall 63 of the housing 54.

Figure 14:
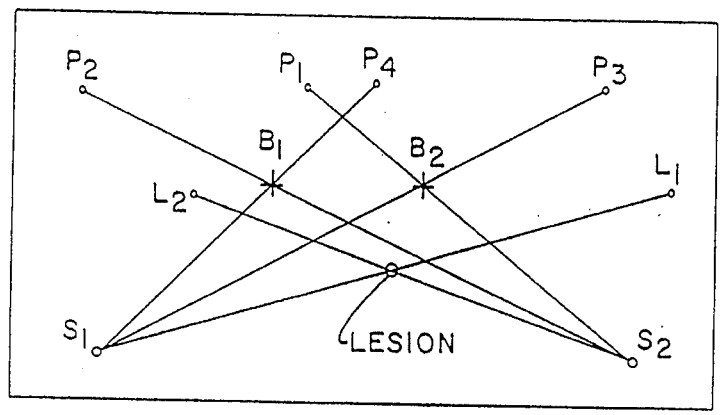
FIG. 14 is a schematic diagram illustrating the stereotactic images employed to identify the coordinates of the target lesion with the imaging system of FIG. 13.

Positioned at points B1 and B2 on the X-ray transparent fixed compression plate 53, in the prior art fixed image receptor of FIG. 13, are X-ray opaque index marks which may take the form of cross hairs as indicated in FIG. 14. These index marks are imaged as shown by the crosses B1 and B2 in FIG. 14, which comprises a vertical projection of the various points along the path of the X-rays proceeding through the system shown schematically in FIG. 13. Thus the point S1 in FIG. 14 corresponds to the vertical projection on the image plane of the source position 28E at which the tubehead 228 is first angularly offset, as indicated in FIGS. 4 and 13. In the same manner, point S2 on the image plane is the vertical projection of the second tubehead source position 28F shown in FIGS. 4 and 13.

The X-ray path from point 28E through X-ray opaque index B1 is imaged at point P4 on the image plane, while at the second source position 28F the X-ray passing through index point B1 is imaged at point P2 as indicated in the vertical projection diagram of FIG. 14, and these two X-ray paths projected on the image plane cross at the index point B1 shown in FIG. 14. In the same manner, index point B2 is determined by the crossing of the vertical projections of the X-ray paths S2P1 and S1P3.

As also indicated in FIG. 14, the X-ray path from source S1 through lesion 51 creates the vertical projection X-ray path S1L1 on the image plane and the crossing of this projected line with line S2L2 indicates the position at which the lesion appears in the stereo projection of FIG. 14. When the coordinates of these points S1, S2, B1, B2 and L1 and L2 are determined on the image plane, this data may be recorded digitally and manipulated to provide highly accurate X, Y and Z coordinates for the actual position of the lesion.

This digital data handling operation is facilitated by the optical system 32, shown in FIGS. 11, 12 and 15–18. These include the coated underside of the pellicle mirror 59 which serves as a mirror reflecting the image of the image plane phosphor plate 62 toward a second mirror 64, which delivers the reflected image of the phosphor plate 62 to lens 66 of the CCD equipped camera 67.

Thus, as viewed from above looking down in FIG. 15, the image of the phosphor screen 62 is reflected from the underside of pellicle film 59 to the right toward the angularly positioned mirror 64 which then directs it downward toward the lens 66, clearly shown in FIG. 15 overlying the CCD camera 67.

Advantageously the pellicle film's reflective undersurface reflects the visible light image toward the CCD camera, avoiding any diffusion or losses from transmission through the phosphor plate 62. Also, the diagonal positioning of film 59 necessarily requires spacing plate 62 away from X-ray transparent cover plate 60. Phosphor plate 62 thus receives the direct X-rays passing from the tubehead through the target, but most secondary or scattered X-rays produced within the target are lost, leaving a clean, sharp resulting image on plate 62.

The camera, operating in the snapshot mode, integrates the image from the phosphor plate 62 and at the end of the exposure, the image is stored in computer memory. This operation is performed for the image produced by X-ray source position 1 at tubehead position 28E, and it is then repeated for source position 2 at tubehead position 28F and another exposure is made. Thus in a few seconds, two stereo pair images are obtained and stored in the computer. The operator then brings the images to the monitor and using a track ball, places cursor locators on the calibration marks B1 and B2 and on the lesion.

Based on the position of these cursors on the monitor screen, the computer then calculates the X, Y and Z location of the lesion relative to the breast compression paddle 38 and plate 53.

These X, Y and Z coordinates may be used immediately for fine needle or core biopsy, using the needle guide to direct the biopsy needle to the site of the lesion, where two more stereo images are recorded to confirm the accurate positioning of the needle tip at the lesion site. Alternatively, these images may also be employed to guide surgery if desired.

Figure 16:
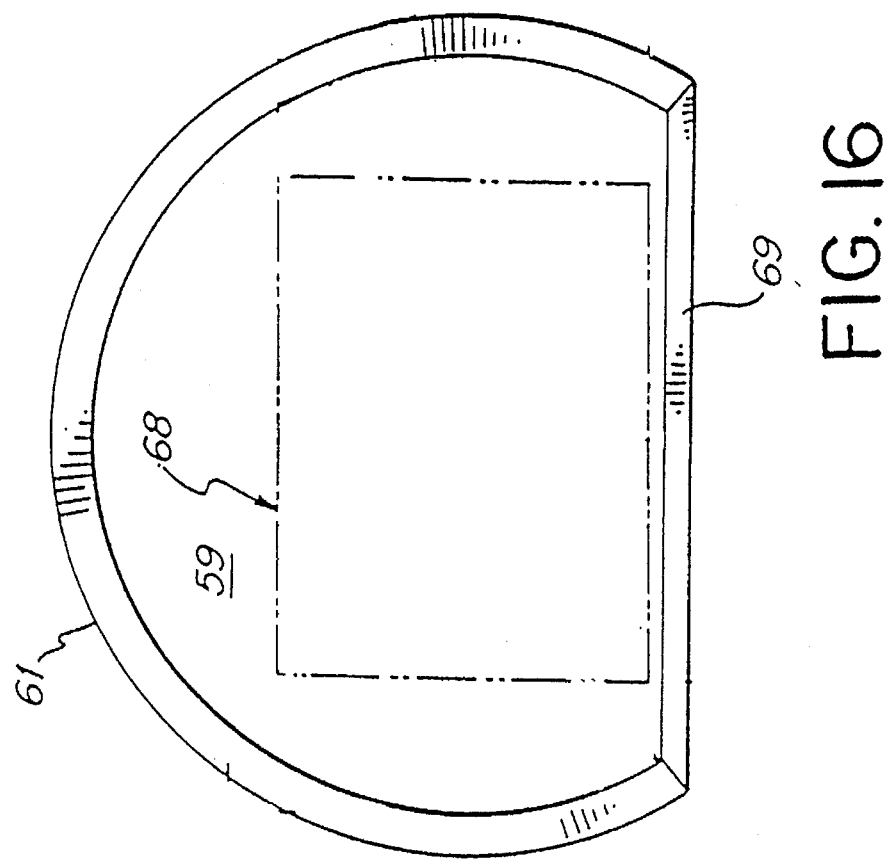
FIG. 16 is a top plan view of the thin film pellicle mirror employed in the optical system of FIG. 15.

The pellicle film thickness preferably falls between five and nine micrometers, and most desirably falls within the range of six to seven micrometers, with the thickness uniformity being accurate and the faces of the film being parallel within two wavelengths of X-radiation per inch. A coating of aluminum and silicon dioxide on the underside of the pellicle film provides a reflectance greater than 8%, with no pinholes being visible to the unaided eye, thus assuring the uniformity of the resulting CCD image. While normal pellicle mirror frames 61 are ring shaped, the unique "D-shaped" configuration of the pellicle mirror 59 and frame 61 in the optical systems of the preferred embodiments of the invention provide a unique advantage: the rectangular area 68 corresponding to the pellicle film reflection of the phosphor plate 62 is uniformly smooth and flat over its entire surface and it will be noted that the circular sector of frame 61 subtends approximately 250 degrees, while the straight chord 69 closing the D-shaped frame 61 subtends the remaining angle of about 110 degrees. This D-shaped frame 61 thus brings the critical area 68 very close to the adjacent chord segment 69 of frame 61, as shown in FIG. 16. Chord segment 69 is positioned closely adjacent to upper housing panel 57, as can be observed in FIG. 15, thus bringing the critical area for imaging X-radiation passing through the patient's breast 52 close to table platform 22, and producing a visible image on the phosphor plate 62 in close juxtaposition with upper housing panel 57, which is positioned vertically as close as possible to the patient's chest wall. By this means, the maximum volume of the patient's breast 52 is exposed to the mammographic examination using the X-radiation passing through the D-shaped pellicle mirror 59.

FIGS. 7A–7C, 11 and 12 show the preferred embodiment of the invention in which the light-tight housing 54 is independent of fixed compression plate 53 and is mounted for pivoting movement on the C-arm with tubehead 28 about a pivot axis 29 spaced slightly away from fixed compression plate 53. Tubehead 28 and housing 54 thus pivot together as a unit, from position 28E–54E in FIG. 18 to position 28F–54F in FIG. 19. A substantial portion of the patient's breast 52 can then be viewed in each position, in a wide image utilizing virtually the full width of phosphor plate 62, as shown in these figures. As soon as CCD camera 67 has recorded the image produced by tubehead 28E, X-ray source S1, the C-arm 27 can be swung to tubehead position 28F, source S2, and the entire width of phosphor plate 62 is again available to receive the second stereo image.

FIGS. 11 and 12 show a second feature characterizing this embodiment: the X-ray opaque index marks B1 and B2, like reference hole 40, are positioned on movable compression paddle 38, rather than on fixed compression plate 53, to assure that diverging radiation paths from either source position passing through the index marks will fall within the useful image area of phosphor plate 62.

CCD DIGITAL IMAGING OPTICAL SYSTEM

Figure 19:
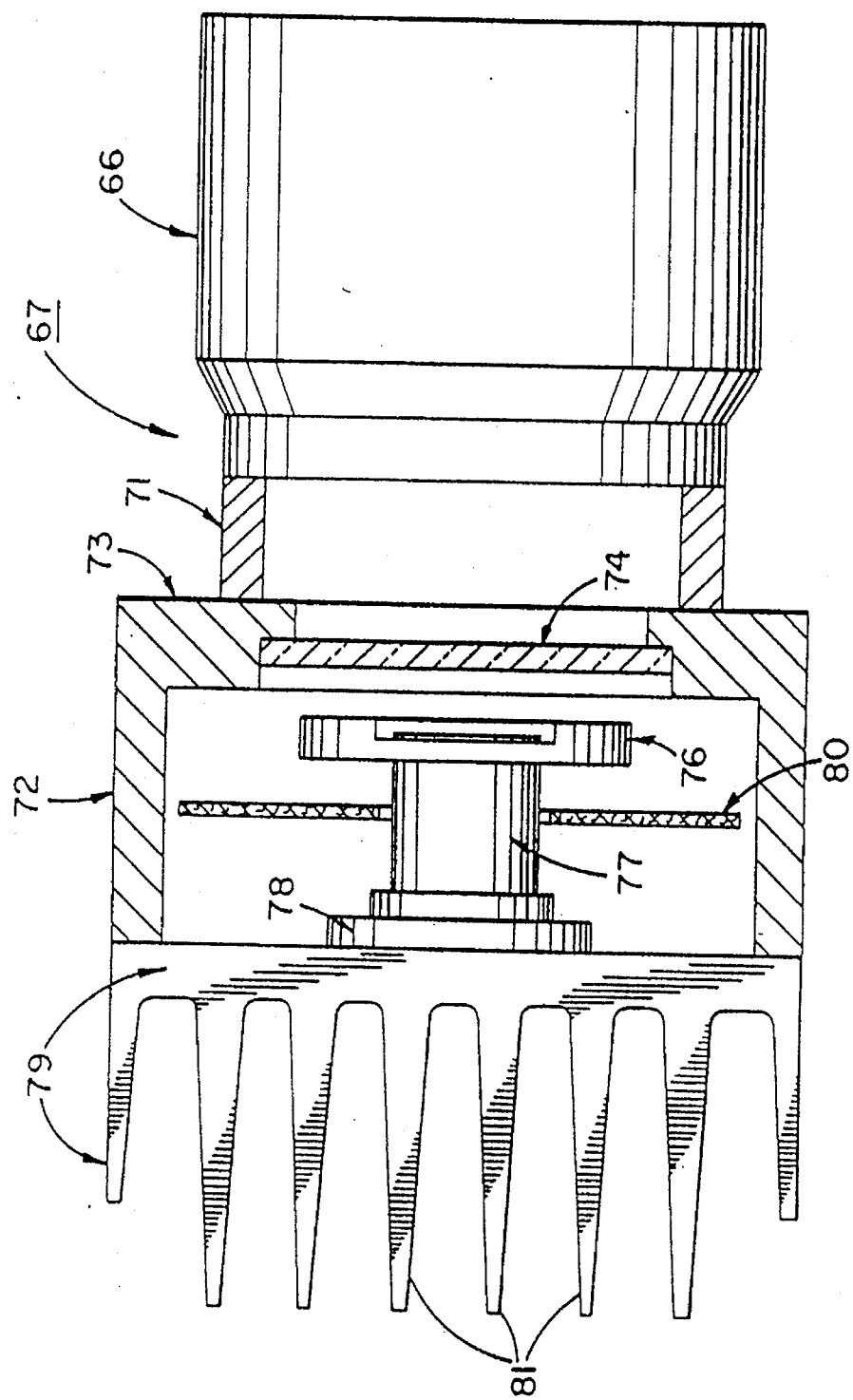
FIG. 19 is a detailed schematic diagram of a preferred form of CCD camera employed in the optical system of FIG. 15.

The preferred form of CCD Camera 67 is shown schematically in more detail in FIG. 19. In this diagram, lens 66 is supported on a lens mount 71 positioned on the front face 73 of camera body 72. Face 73 incorporates a light-transparent window 74 behind which CCD array 76 is positioned. Light focused by lens 66 is delivered through window 74 to a focal plane corresponding to the face of CCD array 76.

Array 76 is mounted on the front end of a "cold finger" pedestal 77 whose rear end is anchored to a Peltier thermoelectric cooler 78 mounted on the camera body's rear face 79 with heat-transfer fins 81 extending into the ambient atmosphere. A ring-shaped printed circuit board 80 closely encircles "cold finger" pedestal 77, minimizing resistance losses in the conductors (not shown in FIG. 19), connecting CCD array 76 to board 80.

CCD array 76, positioned at the focal plane of lens 66, receives a focused image of the light produced by phosphor plate 62 via mirrors 59 and 64, and the array is quickly scanned, facilitating the storing of the image in memory for manipulation, enhancement and future study as desired, without any delays such as those required for processing of X-ray film.

Figure 18:
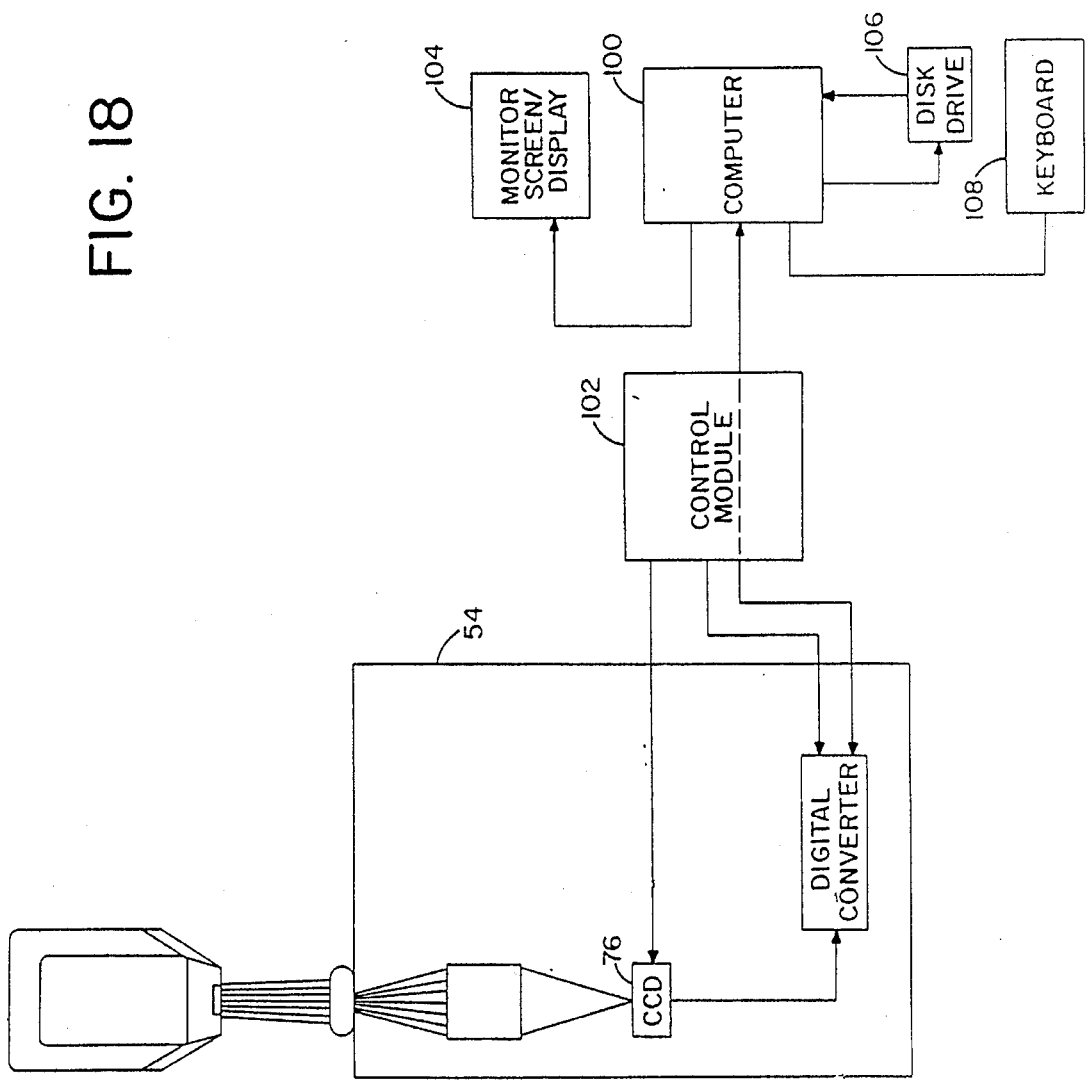
FIG. 18 is a schematic diagram showing the imaging of the patient's compressed breast on a phosphor plate in the optical system delivering a focussed image to the CCD sensor and the processing of the CCD output signals through the image enhancement computer to the monitor screen display.
Figure 20:
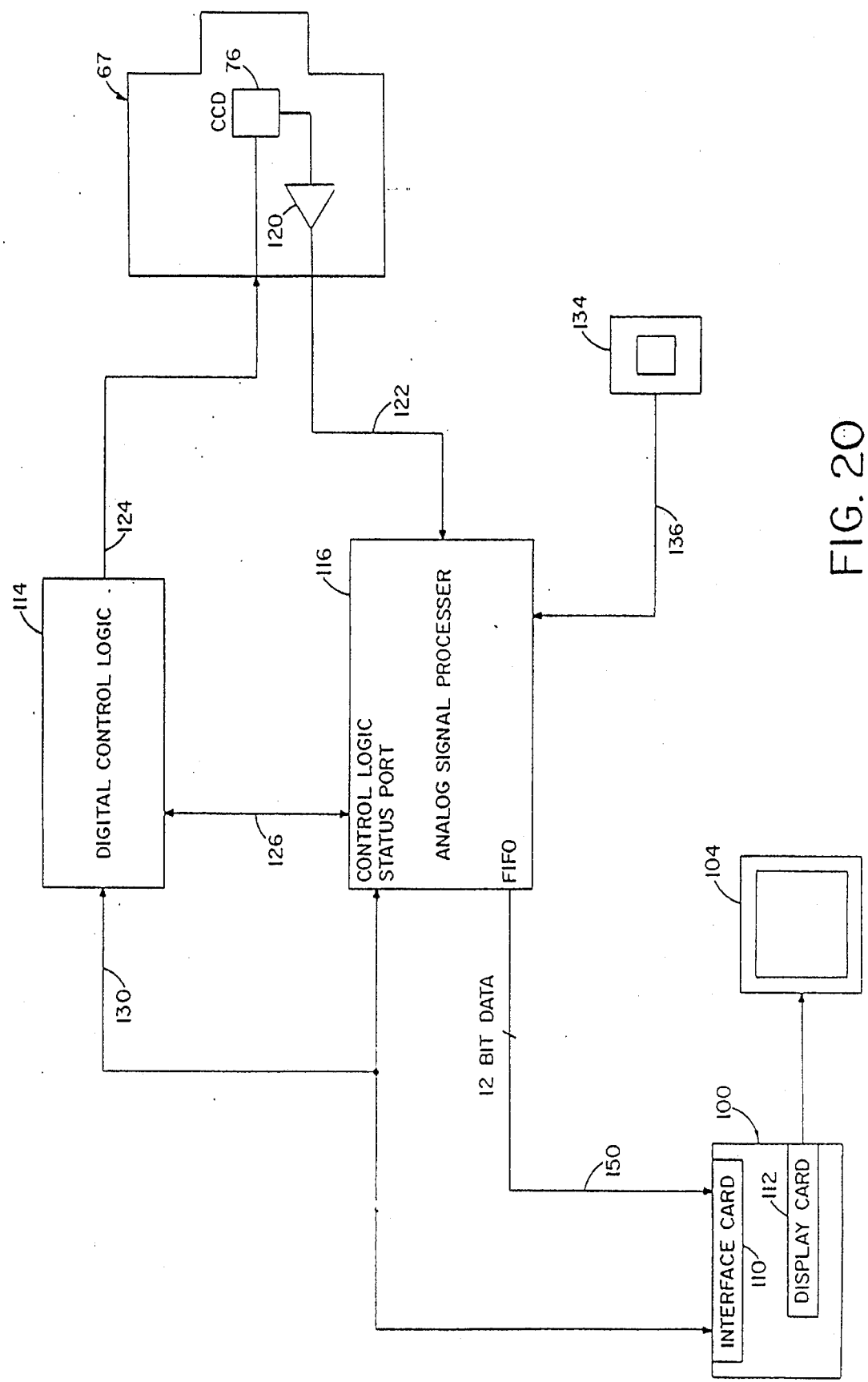
FIG. 20 is an overall block diagram of the system electronics used to convert the digital information from the CCD camera into mammographic display information as presented on the monitor driven by an associated computer.

As best seen in FIGS. 18 and 20, the computer and associated system electronics forming part of the overall digital mammography system comprises computer 100, a control module 102, a module 104 fore presentation of mammography information, disc drive 106 and keyboard 108 associated with computer 100. As best seen in FIG. 20, the system electronics include an interface card 110 and a video display card 112 which reside within computer 100.

Details concerning the computer, video card and monitor used in the preferred embodiment of the present invention are presented in Table 1.

TABLE 1

| Computer 100 | IBM compatible personal computer with an Intel type 80386 ™ or 80486 ™ procesor and 12 to 16 Mb RAM, and 200 MB hard disk storage |
|---|---|
| Video display card 112 | Trident Impact 3 ™ video display card with 1024 × 768 pixel resolution and 8 bit luminance resolution per pixel |
| Monitor 104 | Dotronix M2400 ™ 20 inch monochrome monitor with P104 phosphor, set to vertical and horizontal scan rate of video card; analog input. |

A digital control logic module 114 and an analog signal processor 116 form the overall control module 102. The digital control logic module generates various clocking signals for transfer to the camera 67 for use by CCDs 76. The output of the CCDs are applied through a preamplifier 120 so as to generate a CCD output signal on a bus 122 for presentation to the analog signal processor 116.

Figure 21:
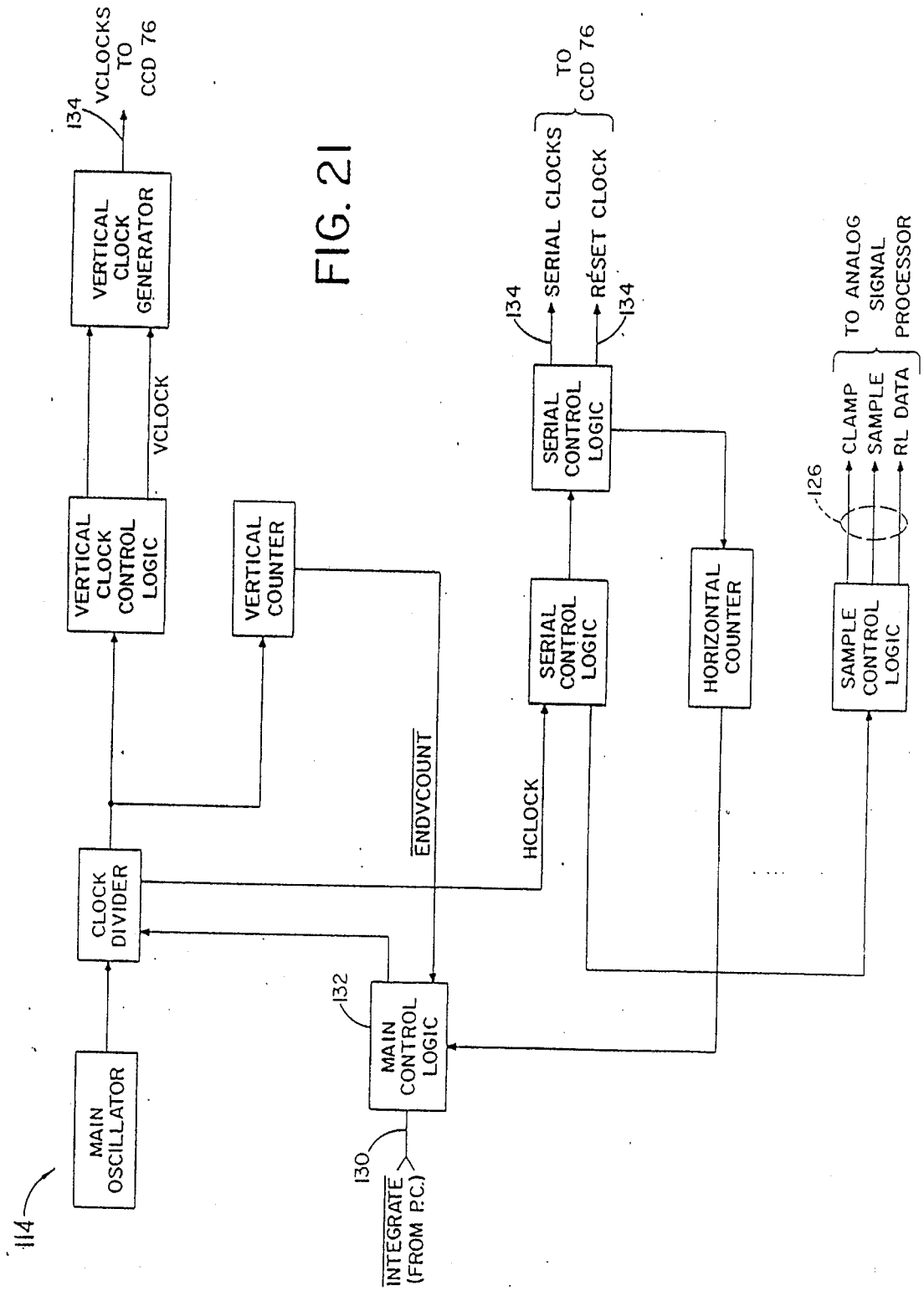
FIG. 21 is a detail block diagram of the digital control logic module shown in FIG. 20.

FIG. 21 is a detailed block diagram of the digital control logic module 114 and illustrates the specific clock signals generated on output bus 124 as well as the clamped sample and data transferred between this module and the analog signal processor module 116 on output bus 126. An integrate control signal from the computer is also shown received on line 130 to the main control logic module 132.

Figure 22:
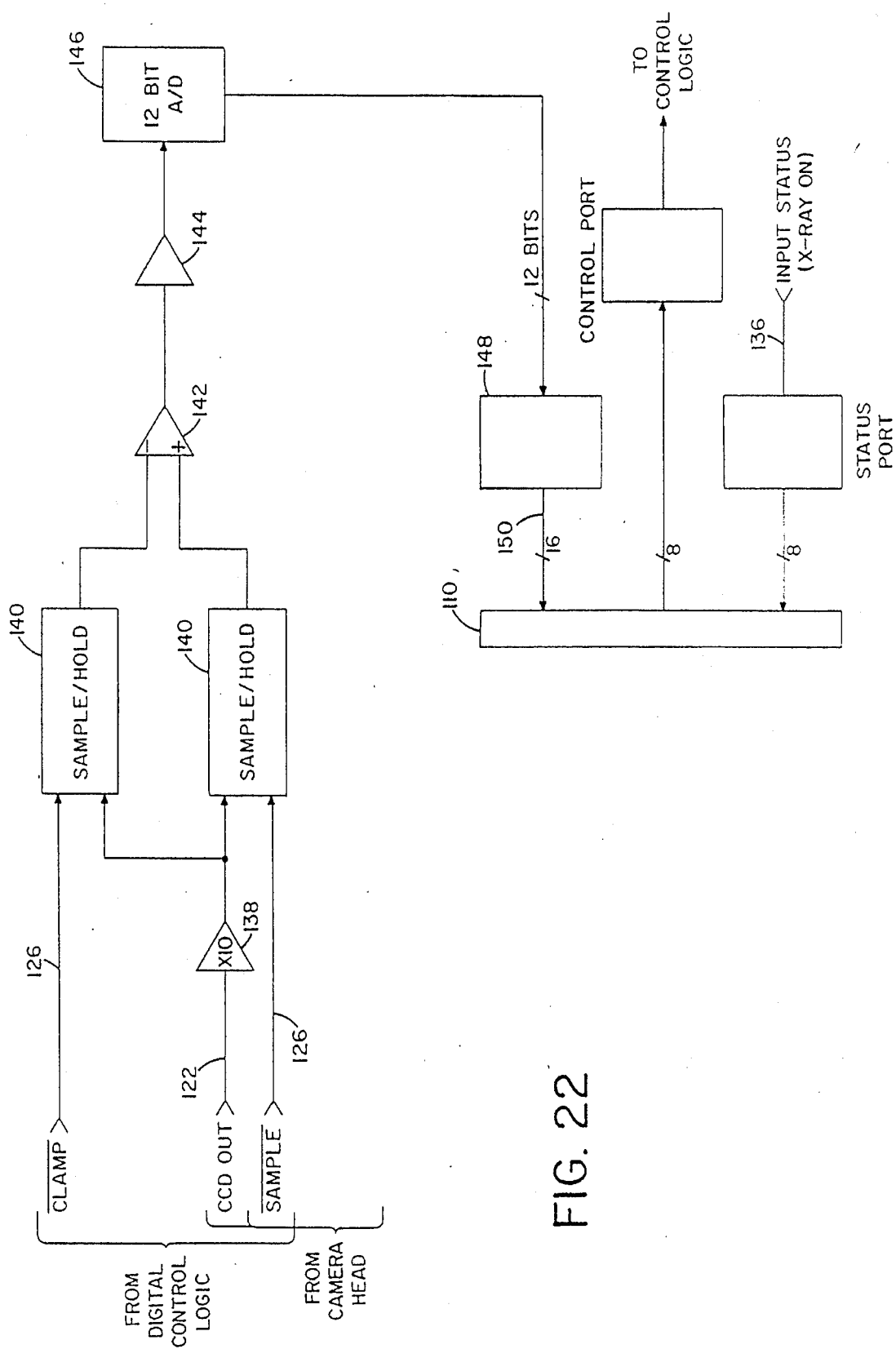
FIG. 22 is a detail block diagram of the analog signal processor module shown in FIG. 20.

Details of the analog signal processor module 116 are shown in the detail block diagram of FIG. 22. As seen in FIGS. 20 and 22 an X-ray status signal indicating the presence of X-rays from X-ray detector 134 is presented on input status line 136.

As can generally be seen in FIG. 22, the CCD output signal received on line 122 is presented to an input amplifier 138 and from there presented under control of the clamp and sample signals to two sample and hold modules 140 and from there to differential amplifier 142 and buffer 144 so as to be presented to a 12 bit analog digital converter 146 so as to present the digital output of the CCD image to a first in first out (FIFO) memory 148. The output of the FIFO memory is connected to the computer interface card 110 for display and image processing by the computer so as to present via display card 112 an output image onto monitor 104. (See FIGS. 18–20).

Figure 23:
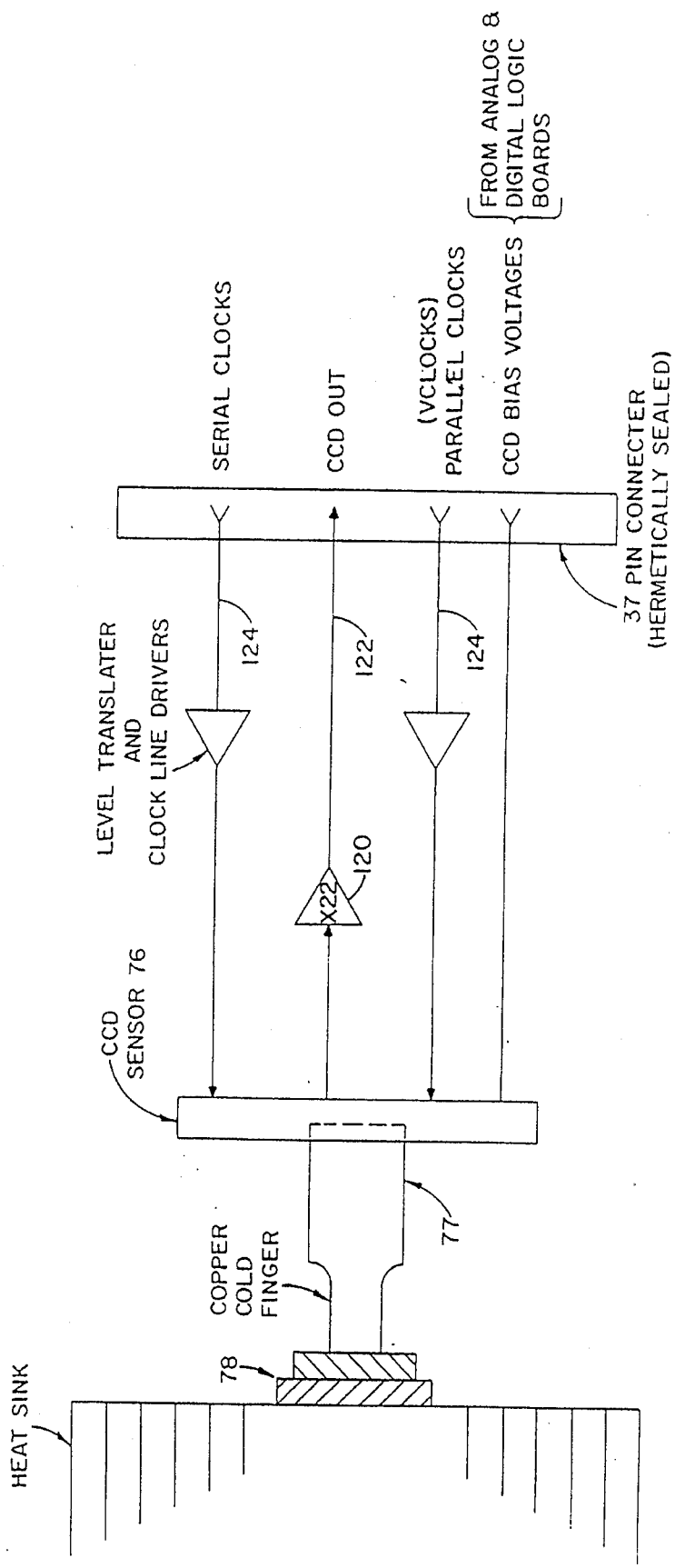
FIG. 23 is an overall diagrammatic view of the CCD camera and its associated electronics.

FIG. 23 is a detailed diagrammatic view of the camera 67 and its associated electronics illustrating the serial clock inputs from the digital control logic module 114 via bus 124; the output of CCD digital data via bus 122; the input of V clocks (parallel clock) information on bus 24; as well as bias voltages from the analog and digital control logic modules 114 and 116.

DIGITAL IMAGE PROCESSING

The overall imaging system shown in FIG. 20 provides an image of the mammographic information on display monitor 104. In order to accomplish this task, the digitized CCD data received on bus 150 from FIFO memory 148 (see FIG. 22) is under the control of computer 100 via execution of a computer program as set forth in a program listing Table 2. As seen in Table 2, the program for achieving mammographic display as well as digital image processing of the mammographic information is written in Microsoft Corporation assembly language as well as Microsoft "C" high level language.

In general, the image presented on monitor 104 comprises 512×512 pixels of mammographic information on a video display of 1024×768 pixels, with each pixel having a luminance resolution of 8 bits or 256 luminance values. The present invention can also support a pixel size display up to 1,024×1,024 pixels. The value of the luminance from the CCD camera has a resolution of 12 bits or 4,096 luminance values. Of course, the 12-bit luminance information from the CCD camera could be displayed with use of a video display card and monitor having such higher luminance imaging capability.

The CCD camera can output data in a 512×512 pixel array or in a 1024×1024 pixel array. If the higher resolution array is used, monitor 104 displays a 1024×768 portion of the CCD data with 128 rows at the top and bottom of the CCD image typically masked; although the viewed image can be scrolled throughout the CCD image.

OVERALL OPERATION OF DIGITAL IMAGE PROCESSING

The computer program listing set forth in table 1 basically performs the following steps in its display of mammographic information: (1) generates 12 bit luminance information for each pixel in the overall display area via subtracting a dark field and removing fixed pattern noise associated with the particular CCD imaging device, (2) divides the dark field by a white field sometimes referred to as "flat fielding" so as to even out any unevenness in the luminance X-ray information as a result of non-uniform X-ray beam illumination, and (3) produces a luminance histogram of the displayed data.

In addition, the digital image processing of the present invention allows for increasing the contrast which effectively narrows the luminance window as well as providing movement of the luminance window with regard to the luminance range of values for which proportional gray-scaling is implemented; that is to move the window with respect to the CCD luminance values of 0 to 4,095. This function is sometimes referred to as "windowing". More particularly, the contrast displayed on monitor 104 can be increased by reducing the luminance values that are displayed. For example, the luminance values from 1,000 to 1,511 could be displayed out of all luminance values from 0 to 4,095. Then, the 512 different luminance values (1,511–1,000 =512) could be mapped into the 256 brightness values displayable on monitor 104 from white for luminance value equal to 1,000 to black for luminance value equal to 1,511. All luminance values equal to or below 1,000 would be displayed as white and all those equal to or above 1511 would be displayed as black. Of course, the luminance values from the CCD camera could be inversely displayed on the monitor. For the example above, all luminance values equal to or less than 1,000 could be displayed as black, and vice versa for luminance values equal to or greater than 1511. It should also be noted that rapidly inverting the displayed data can help the operator to see features of the image than otherwise possible if only one video polarity is displayable.

Windowing is the ability to slide the range of values to be displayed up or down the luminance 4,096 values from the CCD camera. In the example above, the 512 different luminance values displayable on monitor 104 could be slid down so as, for example, to include pixel luminance values from 70 to 581, or slid upward, to include pixel luminance values from 4,020 to 4,531, for example. This combination of constant control and windowing provide significant diagnostic imaging improvement for the original CCD imaging data received from the camera.

Figure 24:
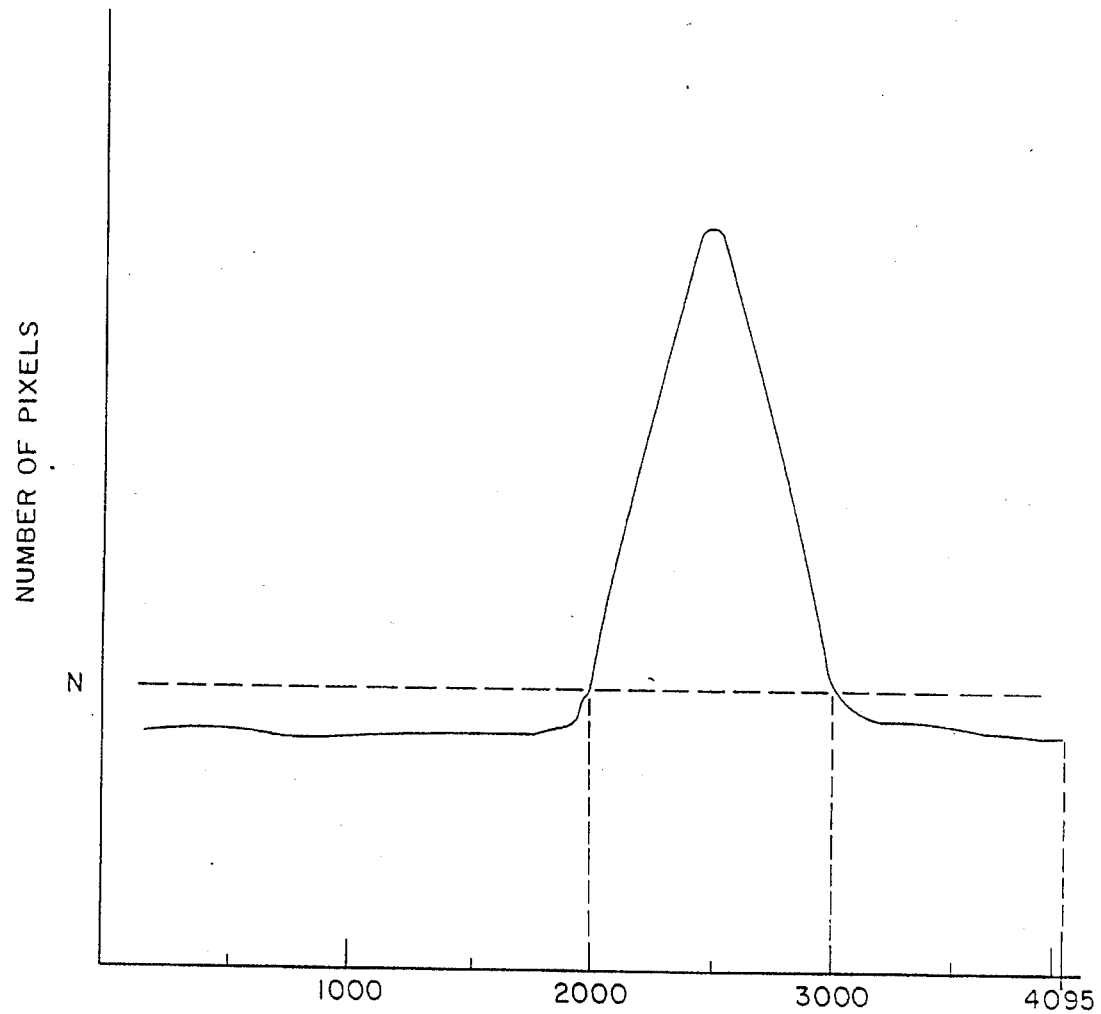
FIG. 24 is a diagram illustrating the number of pixels of an overall typical image which have particular luminance values.

Furthermore, a luminance histogram can be produced by the imaging system. This luminance histogram is then used in a process sometimes referred to as auto-gray scaling. In essence, this process analyzes the CCD imaging data to determine what luminance values are predominantly obtained for a particular image. For example, an image might have most pixels at luminance values in a range of 2,000 to 3,000. Typically, the number of pixels at particular luminance values would have a characteristic bell-shape curve such as shown in FIG. 24. The system then determines that the majority of pixel luminance values predominantly lie between 2,000 and 3,000 and thus would display only those values as gray scale on the monitor. Those pixels with luminance values equal to or less than 2,000 would be displayed as white while pixel values equal to or greater than 3,000 would be displayed as black. The process is therefore similar to selecting the luminance values to be displayed for contrast enhancement.

The present invention also incorporates convolution filtering and edge enhancement which can operate on all or a subset of the displayed image. For convolution filtering a kernel having a matrix size of 3×3 pixels or 5 ×5 pixels can be used around each pixel for which such convolution filtering is desired.

Furthermore, the implementation uses a lookup table technique for the gray scale associated with the screen luminance and thus provides a luminance to gray scale image mapping as described above.

Additional features also include a high pass filtering so as to sharpen details as well as low pass filtering so as to remove high spatial noise which effectively provides for edge enhancement for rapidly changing data.

Furthermore, the present invention can perform "histogram equalization" and "contrast stretching". Similar to the convolution filtering described above, these functions can operate on all or a subset of the displayed image, sometimes referred to as the region of interest. "Contrast stretching" effectively stretches the grayscale over the region of interest, thereby using the entire available range of displayable grayscale only in this region of interest.

In "histogram equalization", the system remaps the data in the region of interest so that the resulting data has an equal number of occurrences for each histogram bin. In other words, if one looked at the luminance histogram in the region of interest after doing histogram equalization, each bar of the histogram would have the same height rather than the bell shape curve as shown in FIG. 24. Histogram equalization helps to enhance the grayscale rendition for certain image making visualization of abnormalities easier.

Finally, the stereotactic imaging explained above uses cursor marking of the displayed image and is implemented in the program listings found in Table 2 of related U.S. Pat. No. 5,289,520, which is incorporated herein by reference. Positioned information in digital form interfaces with the X, Y or Z control knobs on the needleguide stage or carriage 45 (FIGS. 6, 7) actuated manually or servodriven, and a null indication signals matching of calculated with actual coordinates. This interfacing corresponds to the manual calculation of coordinates using a "digitizing pad" with a film grid system like those used with computer pads, to produce the same matching with the actual coordinates of the needle guide stage.

The overall operation of the various program modules are explained via the comments associated with those modules in program listing found in Table 2 of related U.S. Pat. No. 5,289,520. The overall result is not only to present the digitized information but to provide for overall enhancement of the information including zooming of specific regions of interest, edge enhancement, contrast enhancement as well as artifact removal associated with the CCD imaging sensors. In general, the digital image processing provides much greater information to the examining physician than that available using radiographic imaging.

It will thus be seen that the objects set forth above, and those made apparent from the preceding descriptions, are efficiently attained and, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A patient-supporting table for performing prone stereotactic mammographic biopsy procedures, the table comprising:

a platform having a first end, a second end, and a breast-receiving aperture permitting pendulant presentation of a patient's breast therethrough, wherein the breast-receiving aperture is positioned on the platform so as to divide the platform into a first supporting portion extending from the first end to the breast-receiving aperture for supporting at least a patient's torso and legs in a first patient position and a second supporting portion extending from the second end to the breast-receiving aperture for supporting at least a patient's torso and legs in a second patient position.

whereby supporting a patient on the first supporting portion of the platform in the first patient position enables the patient's breast to be pendulantly presented in a first orientation through the breast-receiving aperture of the platform and whereby supporting a patient on the second supporting portion of the platform in the second patient position enables the patient's breast to be pendulantly presented in a second orientation through the breast-receiving aperture of the platform.

2. The patient-supporting table of claim 1 further comprising a concave torso depression surrounding the aperture in the platform.

3. The patient-supporting table of claim 1, wherein the first supporting portion of the platform is provided with an extensible and retractable footrest, and the second supporting portion of the platform is provided with an extensible and retractable footrest.

4. A prone stereotactic mammographic biopsy apparatus for performing stereotactic X-ray guided breast biopsies comprising:

a base;

a pedestal extending upwardly from the base:

a platform supported by the pedestal, the platform having a first end, a second end, and a breast-receiving aperture permitting pendulant presentation of a patient's breast therethrough, wherein the breast-receiving aperture is positioned on the platform so as to divide the platform into a first supporting portion extending from the first end to the breast-receiving aperture for supporting at least a patient's torso and legs in a first patient position and a second supporting portion extending from the second end to the breast-receiving aperture for supporting at least a patient's torso and legs in a second patient position;

a positionable ledge extending outwardly from the pedestal below the patient-supporting platform;

means for obtaining stereotactic X-ray images of the patient's breast pendulantly presented through the breast-receiving aperture in the patient-supporting platform, the means being supported by the positionable ledge;

means for compressing the pendulantly presented breast, the means being supported by the positionable ledge; and means for guiding a biopsy needle into the pendulantly presented and compressed breast, the means being supported by the positionable ledge;

whereby supporting a patient on the first supporting portion of the platform in the first patient position enables a patient's breast to be pendulantly presented through the breast-receiving aperture in a first orientation with respect to the breast-receiving aperture and means for obtaining stereotactic X-ray images, means for compressing the breast and means for guiding a biopsy needle, and whereby supporting a patient on the second supporting portion of the platform in the second patient position enables the patient's breast to be pendulantly presented through the breast-receiving aperture in a second orientation with respect to the breast-receiving aperture and means for obtaining stereotactic X-ray images, means for compressing the breast and means for guiding a biopsy needle.

5. The apparatus of claim 4, further comprising a concave torso depression surrounding the aperture in the platform.

6. The apparatus of claim 4, wherein the first supporting portion of the platform is provided with an extensible and retractable footrest, and the second supporting portion of the platform is provided with an extensible and retractable footrest.

7. The apparatus of claim 4, wherein the pedestal includes means for adjusting the height of the platform relative to the base.

8. The apparatus of claim 4, wherein the means for obtaining stereotactic X-ray images, means for compressing the pendulantly presented breast and means for guiding a biopsy needle have a range of rotation relative to the breast-receiving aperture of at least 180° and less than 360° as measured from an axis extending from the first end of the platform to the second end of the platform.

9. A method for using a prone stereotactic guided needle breast biopsy apparatus to sample an area of interest in a breast, the method comprising the steps of:

(a) providing a prone stereotactic guided needle breast biopsy apparatus, the apparatus further comprising:

a base, a pedestal extending upwardly from the base, a platform supported by the pedestal, the platform having a first end, a second end, and a breast-receiving aperture pertaining pendulant presentation of a patient's breast therethrough, wherein the breast-receiving aperture is positioned on the platform so as to divide the platform into a first supporting portion extending from the first end to the breast-receiving aperture for supporting at least a patient's torso and legs in a first patient position and a second supporting portion extending from the second end to the breast-receiving aperture for supporting at least a patient's torso and legs in a second patient position, a positionable ledge extending outwardly from the pedestal below the platform, means for obtaining stereotactic X-ray images of the patient's breast pendulantly presented through the breast-receiving aperture in the platform, the means being supported by the positionable ledge, means for compressing the pendulantly presented breast, the means being supported by the positionable ledge, and means for guiding a biopsy needle into the pendulantly presented and compressed breast, the means being supported by the positionable ledge, wherein supporting a patient on the first supporting portion of the platform in a first patient supporting position enables the patient's breast to be pendulantly presented through the breast receiving aperture in a first orientation with respect to the breast-receiving aperture, the means for obtaining stereotactic X-ray images, the means for compressing the breast and the means for guiding a biopsy needle by positioning, and whereby supporting a patient on the second supporting portion of the platform in a second patient supporting position enables the patient's breast to be pendulantly presented through the breast-receiving aperture in a second orientation with respect to the breast-receiving aperture, the means for obtaining stereotactic X-ray images, the means for compressing the breast and the means for guiding a biopsy needle;

(b) determining the approximate location of the area of interest in a patient's breast;

(c) determining whether the first orientation or the second orientation of the pendulantly presented breast enables biopsy needle access to the area of interest with a minimal needle path length from the needle guiding means;

(d) positioning the patient on the platform to enable biopsy needle access to the area of interest with a minimal needle path length from the needle guiding means in accordance with the determination in step (c);

(e) compressing the pendulantly presented breast so as to obtain a compressed pendulantly presented breast;

(f) imaging the compressed pendulantly presented breast so as to obtain stereotactic images of the area of interest therein;

(g) determining the three dimensional location of the area of interest from the stereotactic images thereof obtained in step (f); and (h) inserting a biopsy needle into the compressed pendulantly presented breast at the three dimensional location determined in step (g) so as to obtain a sample of breast tissue in the area of interest.

10. A method for using a prone stereotactic guided needle breast biopsy apparatus to sample an area of interest in a breast, the method comprising the steps of:

(a) providing a prone stereotactic guided needle breast biopsy apparatus, the apparatus further comprising:

a base, a pedestal extending upwardly from the base, a platform supported by the pedestal, the platform having a first end, a second end, and a breast-receiving aperture permitting pendulant presentation of a patient's breast therethrough, wherein the breast-receiving aperture is positioned on the platform so as to divide the platform into a fast supporting portion extending from the first end to the breast-receiving aperture for supporting at least a patient's torso and legs in a first patient position and a second supporting portion extending from the second end to the breast-receiving aperture for supporting at least a patient's torso and legs in a second patient position, a positionable ledge extending outwardly from the pedestal below the platform, means for obtaining stereotactic X-ray images of the patient's breast pendulantly presented through the breast-receiving aperture in the platform, the means being supported by the positionable ledge, means for compressing the pendulantly presented breast, the means being supported by the positionable ledge, and means for guiding a biopsy needle into the pendulantly presented and compressed breast, the means being supported by the positionable ledge, wherein supporting a patient on the first supporting portion of the platform in a first patient supporting position enables the patient's breast to be pendulantly presented through the breast receiving aperture in a fast orientation with respect to the breast-receiving aperture, the means for obtaining stereotactic X-ray images, the means for compressing the breast and the means for guiding a biopsy needle by positioning, and whereby supporting a patient on the second supporting portion of the platform in a second patient supporting position enables the patient's breast to be pendulantly presented through the breast-receiving aperture in a second orientation with respect to the breast-receiving aperture, the means for obtaining stereotactic X-ray images, the means for compressing the breast and the means for guiding a biopsy needle;

(b) determining the approximate location of the area of interest in a patient's breast;

(c) determining whether the first orientation or the second orientation of the pendulantly presented breast enables biopsy needle access to the area of interest from the underside of the breast;

(d) positioning the patient on the platform to enable biopsy needle access to the area of interest from the underside of the breast in accordance with the determination made in step (c);

(e) compressing the pendulantly presented breast so as to obtain a compressed pendulantly presented breast;

(f) imaging the compressed pendulantly presented breast so as to obtain stereotactic images of the area of interest therein;

(g) determining the three dimensional location of the area of interest from the stereotactic images thereof obtained in step (f); and (h) inserting a biopsy needle into the compressed pendulantly presented breast at the three dimensional location determined in step (g) so as to obtain a sample of breast tissue in the area of interest from the underside of the breast.

* * * * *